United States Patent [19]

Pedrazzi

[11] Patent Number: 4,686,285

[45] Date of Patent: Aug. 11, 1987

[54] BASIC AZO AND NON-AZO COMPOUNDS HAVING ONE OR TWO DISUBSTITUTED 1,3,5-TRIAZINE RINGS EACH OF WHICH IS LINKED THROUGH A BRIDGING RADICAL TO THE 1-POSITION OF A PYRAZOLE RING

[75] Inventor: Reinhard Pedrazzi, Allschwil, Switzerland

[73] Assignee: Sandoz Ltd., Basel, Switzerland

[21] Appl. No.: 699,916

[22] Filed: Feb. 8, 1985

[30] Foreign Application Priority Data

Feb. 10, 1984 [DE] Fed. Rep. of Germany ....... 3404778

[51] Int. Cl.$^4$ .................. C09B 31/47; C09B 35/08; C09B 45/26; C09B 44/08
[52] U.S. Cl. ................... 534/606; 162/162; 534/567; 534/582; 534/602; 534/604; 534/608; 534/612; 534/710; 534/728; 534/740; 534/756; 534/760; 534/764; 534/772; 534/775; 534/776; 544/181; 544/198
[58] Field of Search .............. 534/606, 608, 612, 776, 534/604, 567, 602, 710, 740, 764, 772, 775, 759, 728, 760; 544/198, 181

[56] References Cited

U.S. PATENT DOCUMENTS 4,273,707 6/1981 Pedrazzi .................... 534/637 X
4,550,158 10/1985 Doswald et al. .............. 534/612

FOREIGN PATENT DOCUMENTS 0075773 4/1983 European Pat. Off. ........... 534/606
0092520 10/1983 European Pat. Off. ........... 534/606
988909 4/1965 United Kingdom ............... 534/606
1009432 11/1965 United Kingdom ............... 534/606
1027614 4/1966 United Kingdom ............... 534/600

Primary Examiner—Floyd D. Higel
Attorney, Agent, or Firm—Gerald D. Sharkin; Richard E. Vila; Melvyn M. Kassenoff

[57] ABSTRACT (i) Metal-free compounds of the formula

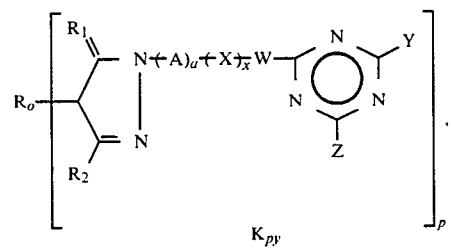

(ii) tautomers thereof,
(iii) 1:1 and 1:2 metal complexes of (i) and (ii),
(iv) salts of (i), (ii), and (iii), and
(v) mixtures of (i), (ii), (iii), and (iv), wherein the symbols are as defined in the Specification, are useful as dyes for, for example, polymers and copolymers of acrylonitrile, polyesters modified to contain acid groups, polyamides such as wool, leather, cotton, bast fibers such as hemp, flax, sisal jute, coir and straw, regenerated cellulose, glass fibers and paper (those wherein $R_o$ is other than hydrogen) or as intermediates for the synthesis of dyes.

20 Claims, No Drawings

BASIC AZO AND NON-AZO COMPOUNDS HAVING ONE OR TWO DISUBSTITUTED 1,3,5-TRIAZINE RINGS EACH OF WHICH IS LINKED THROUGH A BRIDGING RADICAL TO THE 1-POSITION OF A PYRAZOLE RING

The invention relates to heterocyclic compounds containing basic and/or cationic groups suitable for use as dyestuffs and to intermediates for making such dyestuffs.

According to the invention there is provided compounds which, in one of the possible tautomeric forms, correspond to formula I,

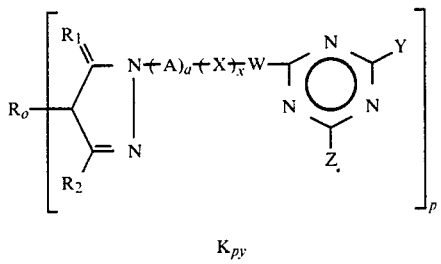

which compounds may be in salt form or acid addition salt form and mixtures of such compounds,
in which
each Y, independently, is hydroxy; amino; $C_{1-4}$alkoxy; phenoxy; an aliphatic, cycloaliphatic, aromatic or heterocyclic amine group or a heterocyclic amine group in which the nitrogen atom is part of the heterocycle which contains one to three hetero atoms and which may be further substituted by up to three $C_{1-4}$alkyl groups; a group Z or a radical which, in one of the possible tautomeric forms, corresponds to formula II,

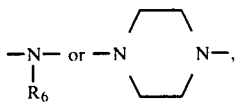

each Z, independently, is an N-bonded organic radical containing 1 to 5 nitrogen atoms of which at least one nitrogen atom has basic character or forms an ammonium cation,
each R, independently, is hydrogen or $D-N=N-$,
each $R_1$, independently, is O, NH or S,
each $R_2$, independently, is $C_{1-4}$alkyl, $C_{1-4}$alkoxy, $-COOR_3$, $-CONR_4R_5$ or $-COZ$,
$R_3$ is hydrogen, $C_{1-4}$alkyl, phenyl or cyclohexyl, each of $R_4$ and $R_5$, independently, is hydrogen; $C_{1-4}$alkyl; $C_{2-4}$alkyl monosubstituted by hydroxy, cyano or chlorine; phenyl or phenyl($C_{1-4}$alkyl), the phenyl group of the latter two substituents being unsubstituted or substituted by one or two groups selected from methyl, ethyl, methoxy and ethoxy; or cyclohexyl,
each a, independently, is 0 or 1,
each x, independently, is 0 or 1, and with the proviso that $a+x$ is 1 or 2;

each A, independently, is phenylene, naphthylene or phenylene-$X_a$-phenylene, in which each of the aromatic rings may be substituted by one or two groups selected from halogen, nitro, $C_{1-4}$alkyl, $C_{1-4}$alkoxy, carboxy and sulpho, $X_a$ is a direct bond or a divalent bridging group,
each X, independently, is a divalent bridging group free from any terminal electron attracting group on the side which is attached to W,
each W, independently, is

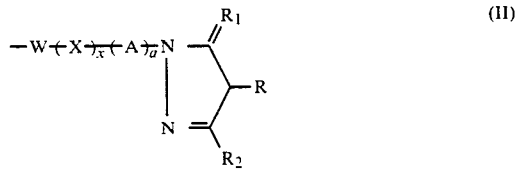

$R_6$ is hydrogen; $C_{1-4}$alkyl; $C_{2-4}$alkyl monosubstituted by hydroxy, cyano, chlorine or $C_{1-4}$alkoxy; phenyl($C_{1-4}$alkyl) or cyclohexyl;
$R_o$ is R or $-N=N-T-N=N-$,
each D, independently, is the radical of a diazo component which may contain further azo groups,
T is the radical of a tetrazo component, and is 1 when $R_o$ is R, and is 2 when $R_o$ is $-N=N-T-N=N-$;
which compounds of formula I are non-azo, monoazo, disazo, trisazo or polyazo compounds, in metal-free or in 1:1 or 1:2 metal complex form and are free from anionic groups or may contain anionic groups in addition to basic and/or cationic groups.

In the specification halogen means fluorine, chlorine, bromine or iodine, preferably fluorine, chlorine or bromine, especially chlorine.

Any alkyl, alkylene or alkenylene present is linear or branched unless indicated otherwise. The alkyl group of any alkoxy group is linear or branched unless indicated to the contrary.

In any hydroxy-substituted alkyl group which is linked to a nitrogen atom, the hydroxy group is bound to a carbon atom other than to the $C_1$-atom.

$R_1$ is preferably O or NH; most preferably it is O.
$R_3$ is preferably $R_{3a}$ where $R_{3a}$ is hydrogen, methyl or ethyl.
$R_4$ and $R_5$ are preferably $R_{4a}$ and $R_{5a}$ where each of $R_{4a}$ and $R_{5a}$, independently, is hydrogen, methyl, ethyl, 2-hydroxyethyl, benzyl or cyclohexyl; most preferably, $R_4$ and $R_5$ are hydrogen.
$R_2$ is preferably $R_{2a}$ where $R_{2a}$ is methyl, ethyl, methoxy, ethoxy, $-COOR_{3a}$, $-CONH_2$ or $-COZ$; more preferably, it is $R_{2b}$ where $R_{2b}$ is methyl, $-COOH$, $-COOCH_3$, $-CONH_2$ or $-COZd$, wherein Zd is defined below; most preferably, $R_2$ is methyl.

A is preferably unsubstituted 1,3- or 1,4-phenylene.
The bridging group X is preferably $C_{1-6}$alkylene, $-C^*ONHC_{1-6}$alkylene or $-S^*O_2NHC_{1-6}$alkylene in which the * denotes the atom attached to the $-(-A-)_a$ group.
a is preferably 1; x is preferably 0.
W is preferably $-NH-$, $-NCH_3-$ or

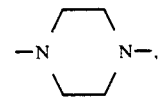

especially $-NH-$.
Z is preferably a group of the formula $$-\underset{\underset{R_7}{|}}{N}\underset{m}{\left(Q_2-\underset{\underset{R_7}{|}}{N}\right)}Q_1-NR_8R_9,$$

$$-\underset{\underset{R_7}{|}}{N}\underset{m}{\left(Q_2-\underset{\underset{R_7}{|}}{N}\right)}Q_1-\overset{\oplus}{N}R_{10}R_{11}R_{12}\ An^{\ominus},$$

$$-\underset{\underset{R_7}{|}}{N}\underset{m_1}{\left(Q_2-\overset{R_7}{\underset{\underset{R_7}{|}}{\overset{|}{\oplus}N}}\right)}Q_1-NR_8R_9m_1\ An^{\ominus},$$

$$-\underset{\underset{R_7}{|}}{N}\underset{m_1}{\left(Q_2-\overset{R_7}{\underset{\underset{R_7}{|}}{\overset{|}{\ominus}N}}\right)}Q_1-\overset{\oplus}{N}R_{10}R_{11}R_{12}m_1+1\ An^{\ominus},$$

$$-N\diagup\diagdown N-Q_3-NR_8R_9,$$

$$-N\diagup\diagdown \overset{\oplus}{N}-Q_3-NR_{10}R_{11}R_{12}\ An^{\ominus},$$

$$-N\diagup\diagdown N-R_{13}\ \text{or}$$

$$-N\diagup\diagdown \overset{R_{13}}{\underset{R_{14}}{\overset{|}{N^{\oplus}}}}\ An^{\ominus},$$

in which
each $R_7$ is independently hydrogen or $C_{1-4}$alkyl, each of
  $R_8$ and $R_9$ is independently hydrogen; $C_{1-6}$alkyl; $C_{2-6}$alkyl monosubstituted by hydroxy or cyano; phenyl($C_{1-3}$alkyl), the phenyl group of which is unsubstituted or substituted by one to three groups selected from chlorine, $C_{1-4}$alkyl and $C_{1-4}$alkoxy; $C_{5-6}$cycloalkyl unsubstituted or substituted by one to three $C_{1-4}$alkyl groups, or
$R_8$ and $R_9$, together with the nitrogen atom to which they are attached, form a 5- or 6-membered saturated or unsaturated ring which contains one to three hetero atoms,
each of $R_{10}$ and $R_{11}$ has independently one of the cyclic or noncyclic significances of $R_8$ and $R_9$ except hydrogen, and $R_{12}$ is $C_{1-4}$alkyl or benzyl, or
$R_{10}$, $R_{11}$ and $R_{12}$, together with the nitrogen atom to which they are attached, form a pyridinium group unsubstituted or substituted by one or two methyl groups,
$Q_1$ is $C_{2-8}$alkylene, $C_{1-6}$alkylene-$C_6$ or $C_{10}$arylene, $C_6$- or $C_{10}$arylene or —N*HCOCH$_2$— where the * denotes the N-atom attached to the —NR$_7$ group;
$Q_2$ is $C_{2-8}$alkylene, $C_{1-6}$alkylene-$C_6$ or $C_{10}$arylene or $C_6$- or $C_{10}$arylene,
$Q_3$ is $C_{2-8}$alkylene, $R_{13}$ is hydrogen or $C_{1-6}$alkyl unsubstituted or monosubstituted by hydroxy, cyano, chlorine or phenyl,
$R_{14}$ is $C_{1-6}$alkyl unsubstituted or substituted by hydroxy, cyano or chlorine,
$m$ is 0 or an integer 1 to 3;
$m_1$ is an integer 1 to 3, and
$An^{\ominus}$ is a non-chromophoric anion.

Any alkyl as $R_7$ is preferably methyl.

$R_7$ is preferably $R_{7a}$ where $R_{7a}$ is hydrogen or methyl; most preferably, $R_7$ is hydrogen.

$R_8$ and $R_9$ are preferably identical. Any $C_{1-6}$alkyl group is preferably $C_{1-4}$alkyl, most preferably methyl or ethyl. Any substituted $C_{2-6}$alkyl group is preferably ethyl or propyl cyano- or hydroxy-substituted in the 2- or 3-position.

Preferably, any phenylalkyl as $R_8$ and $R_9$ is benzyl, the phenyl group of which preferably is further unsubstituted. Any cycloalkyl is preferably cyclohexyl and any alkyl-substituted cycloalkyl is preferably substituted by one to three methyl groups.

Where $R_8$ and $R_9$ together with the nitrogen atom to which they are attached form a ring, they preferably form a pyrrolidine, piperidine, morpholine, piperazine or N-methylpiperazine group.

Preferably, $R_8$ and $R_9$ are $R_{8a}$ and $R_{9a}$ where each of $R_{8a}$ and $R_{9a}$, independently, is hydrogen, linear or branched $C_{1-6}$alkyl, unbranched hydroxy-$C_{2-3}$alkyl or benzyl or both $R_{8a}$ and $R_{9a}$, together with the N-atom to which they are attached, form a pyrrolidine, piperidine, morpholine, piperazine or N-methylpiperazine group.

More preferably, they are $R_{8b}$ and $R_{9b}$ where each of $R_{8b}$ and $R_{9b}$ is hydrogen, linear or branched $C_{1-4}$alkyl or 2-hydroxyethyl or both $R_{8b}$ and $R_{9b}$, together with the N-atom to which they are attached, form a morpholine, piperidine, piperazine or N-methylpiperazine group.

Most preferably, they are $R_{8c}$ and $R_{9c}$, where each of $R_{8c}$ and $R_{9c}$ is methyl or ethyl.

Preferably, $R_{10}$ and $R_{11}$ are identical and signify $R_{10a}$ and $R_{11a}$ where each of $R_{10a}$ and $R_{11a}$ is linear or branched $C_{1-6}$alkyl, unbranched hydroxy-$C_{2-3}$alkyl or benzyl or $R_{10a}$, $R_{11a}$ and $R_{12}$, together with the N-atom to which they are attached, form a pyridinium ring unsubstituted or substituted by one or two methyl groups. More preferably, they are $R_{10b}$ and $R_{11b}$ where each of $R_{10b}$ and $R_{11b}$ is linear or branched $C_{1-4}$alkyl or 2-hydroxyethyl or $R_{10b}$, $R_{11b}$ and $R_{12}$, together with the N-atom to which they are attached, form a pyridinium ring. Most preferably, they are $R_{10c}$ and $R_{11c}$ where each of $R_{10c}$ and $R_{11c}$ is methyl or ethyl.

Any alkyl as $R_{12}$ is preferably methyl or ethyl, especially methyl.

$R_{12}$ is preferably $R_{12a}$ where $R_{12a}$ is methyl, ethyl or benzyl, especially methyl, or $R_{12a}$, $R_{10b}$ and $R_{11b}$, together with the N-atom to which they are attached, form a pyridinium ring.

Any alkylene as $Q_1$, $Q_2$ or $Q_3$ preferably contains 2 to 6 carbon atoms and is linear or branched, e.g., $$-\underset{\underset{CH_3}{|}}{CH}CH_2-,\ -CH_2\underset{\underset{CH_3}{|}}{CH}-\ \text{or}\ -CH_2\underset{\underset{CH_3}{|}}{\overset{\overset{CH_3}{|}}{CH}}CH_2-;$$

more preferably, it is an unbranched $C_{2-6}$alkylene group, especially an ethylene or propylene group; most preferably, it is a linear propylene group.

Any alkylene-arylene as $Q_1$ or $Q_2$ is preferably an alkylene-1,3-phenylene or -1,4-phenylene group containing 7 to 10 carbon atoms; any arylene is preferably 1,3- or 1,4-phenylene.

Preferably, $Q_1$ is $Q_{1a}$ where $Q_{1a}$ is —N*HCOCH$_2$—, linear or branched $C_{2-6}$alkylene, -(CH$_2$)$_{1-4}$-1,3- or -1,4-phenylene or 1,3- or 1,4-phenylene. More preferably, it is $Q_{1b}$ where $Q_{1b}$ is unbranched $C_{2-6}$alkylene; most preferably, it is $Q_{1c}$ where $Q_{1c}$ is ethylene or 1,3-propylene, especially the latter.

$Q_2$ is preferably $Q_{2a}$ where $Q_{2a}$ is one of the significances of $Q_{1a}$ except —N*HCOCH$_2$—. More preferably, it is $Q_{2b}$ where $Q_{2b}$ is unbranched $C_{2-6}$alkylene. Most preferably, it is $Q_{2c}$ where $Q_{2c}$ is ethylene or 1,3-propylene.

$Q_3$ is preferably $Q_{3a}$ where $Q_{3a}$ is linear or branched $C_{2-6}$alkylene. More preferably, it is $Q_{3b}$ where $Q_{3b}$ is linear $C_{2-6}$alkylene. Most preferably, it is $Q_{3c}$ where $Q_{3c}$ is ethylene or 1,3-propylene.

Any alkyl as $R_{13}$ or $R_{14}$ is preferably a $C_{1-4}$alkyl group, especially a methyl or ethyl group; any substituted alkyl is preferably a monohydroxy-substituted $C_{2-4}$alkyl group.

$R_{13}$ is preferably $R_{13a}$ where $R_{13a}$ is hydrogen, $C_{1-4}$alkyl or monohydroxy-substituted $C_{2-4}$alkyl; more preferably, it is $R_{13b}$ where $R_{13b}$ is hydrogen, methyl or ethyl.

$R_{14}$ is preferably $R_{14a}$ where $R_{14a}$ is $C_{1-4}$alkyl or monohydroxy-substituted $C_{2-4}$alkyl. More preferably, it is $R_{14b}$ where $R_{14b}$ is methyl, ethyl, or 2-hydroxyethyl.

m is preferably 0 or 1; more preferably, it is 0.

$m_1$ is preferably 1.

Z is preferably Za where Za is a group of the formula

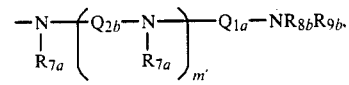

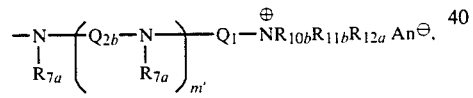

in which m' is 0 or 1,

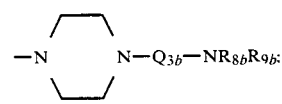

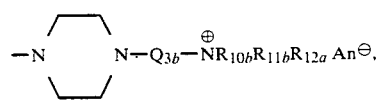

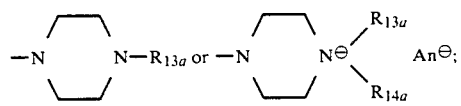

more preferably, it is Zb, where Zb is a group of the formula

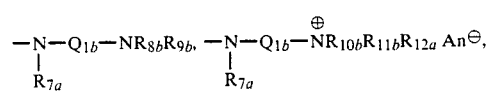

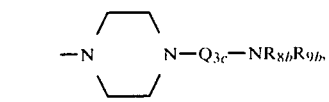

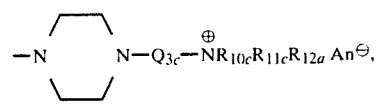

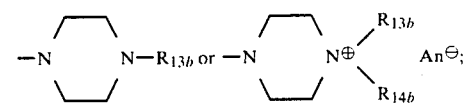

even more preferably, it is Zc where Zc is a group of the formula

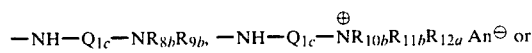

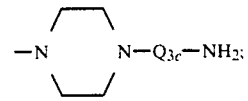

especially it is Zd where Zd is a group of formulae —NH—$Q_{1c}$—NR$_{8c}$R$_{9c}$ or

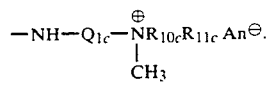

The group of formula II is preferably a group of formula IIa

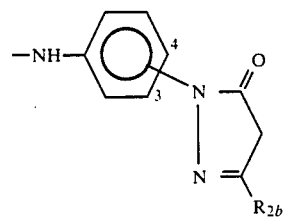

(IIa)

in which the N-atom of the pyrazolone is bound to the 3- or 4-position of the phenyl group.

Any aliphatic amine group as Y is preferably a mono-$C_{1-4}$alkyl- or a di-($C_{1-4}$alkyl)-amino group. The alkyl group may be monosubstituted by halogen, preferably chlorine or bromine, or hydroxy; any cycloaliphatic amine group is preferably $C_{5-6}$cycloalkylamino the cycloalkyl group of which may be substituted by one or two $C_{1-2}$alkyl groups.

Any aromatic amine group as Y is preferably an aniline group, the phenyl ring of which is unsubstituted or substituted by one or two groups selected from halogen (preferably chlorine), $C_{1-4}$alkyl, $C_{1-4}$alkoxy, hydroxy and phenoxy.

In any heterocyclic amine group as Y preferably the N-atom is part of the heterocycle which preferably is a saturated 5- or 6-membered ring which contains one or two hetero atoms and may be further substituted by one or two methyl groups. More preferably, it is a morpholine, piperidine, piperazine or N-methylpiperazine group.

Y is preferably Ya where Ya is hydroxy, methoxy, phenxoy, amino, mono-$C_{1-4}$alkylamino, monohydroxy$(C_{2-4})$alkyl)amino, di($C_{1-2}$alkyl)amino, di($C_{2-4}$hydroxyalkyl)amino, anilino, morpholino, piperidino, piperazino, N-methylpiperazino, Zb or the group of formula II a as defined above. More preferably, it is Yb, where Yb is hydroxy, amino, mono-$C_{1-2}$alkylamino, monohydroxy($C_{2-4}$)alkyl)amino, di($C_{2-4}$hydroxyalkyl)amino or Zc. Most preferably Y is Zd.

Preferred compounds of formula I include
(1) those wherein each $R_1$ is independently O or NH, and each $R_2$ is independently $R_{2b}$,
(2) those of (1) wherein each $R_1$ is O, and each $R_2$ is methyl,
(3) those wherein each A is independently 1,3- or 1,4-phenylene, each W is independently —NH—, —NCH$_3$— or

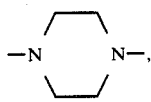

a is 1, and x is 0, and
(4) those wherein each Z is independently Zb.

Preferred compounds of formula I wherein $R_o$ is hydrogen and p is 1 correspond, in one of the possible tautomeric forms, to formula Ia

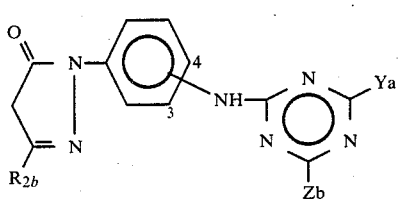

in which the —NH— group is bound to the 3- or 4-position of the phenyl ring. More preferred are compounds of formula Ib being compounds of formula Ia in which $R_{2b}$ is methyl, Ya is Yb and Zb is Zc. Most preferred are compounds of formula Ic being compounds of formula Ia in which $R_{2b}$ is methyl and Ya and Zb both are Zd.

The anions $An^{\ominus}$ can be any non-chromophoric organic or inorganic anions such as those conventional in basic dyestuff chemistry. Suitable anions include chloride, bromide, iodide, lactate, acetate, propionate, citrate, oxalate, malate, maleate, succinate, methylsulphate, ethylsulphate and hydrogensulphate.

The present invention further provides a process for the preparation of compounds of formula I in which $R_o$ is hydrogen and p is 1 comprising reacting a cyanuric halide in any desired order with
a compound of formula III

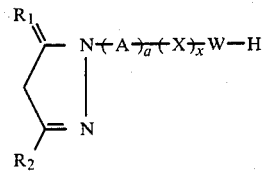

a compound of the formula Z—H, and optionally an inorganic base or a compound of the formula $Y_x$-H where $Y_x$ is —NH$_2$; $C_{1-4}$alkoxy; phenoxy; an aliphatic, cycloaliphatic, aromatic or heterocyclic amine group or a heterocyclic amine group in which the N-atom is part of the heterocycle which contains one to three hetero atoms and which may be further substituted by up to three $C_{1-4}$alkyl groups,
which components must be present in the corresponding stoichiometric molar ratio to obtain a compound of formula I as defined above.

The separate condensation steps to replace the halogen atoms of the triazine are carried out in accordance with known methods.

The compound of the formula Z—H used as a starting material is, for example, one of the followng amines: 2-dimethylaminoethylamine, 3-dimethylaminopropylamine, 3-diethylaminopropylamine, 3-morpholinopropylamine, 2-diethylaminoethylamine, 2-(bis-β-hydroxyethylamino)ethylamine, 3-(bis-β-hydroxyethylamino)propylamine, 4-amino-N,N-di-methylbenzylamine, 3-amino-N,N-dimethylbenzylamine, 1,2-diaminoethane, 1,2-diaminopropane, 1,2-diaminobutane, 1,4-diaminobutane, 2-methylaminoethylamine, diethylenetriamine, bi-(3-aminopropyl)-amine, 2-hydroxyethylpiperazine, 2-aminoethylpiperazine, 1,4-diaminocyclohexane, N-methylpiperazine, piperazine, aniline-3- or -4-trimethylammonium chloride, aniline-3- or -4-methylene-trimethylammonium methylsulphate and 2-aminonaphthalene-5-methylene-trimethylammonium chloride.

The compounds of formula I wherein $R_o$ is hydrogen and p is 1 can also be prepared by coupling to a diazotized compound of formula VII

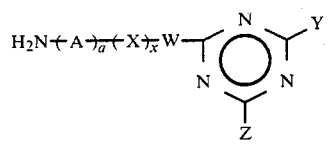

a 2-acylsuccinic acid ester and subsequently closing the ring according to the method described in the European Patent Publication 72 508.

The starting materials used in these processes are either known or may be prepared in accordance with known methods from available starting materials.

The compounds of formula I wherein $R_o$ is hydrogen and p is 1 may be isolated in accordance with conventional methods. They are intermediates for making dyestuffs and are particularly useful as coupling components to prepare azo compounds.

Such azo compounds having formula IV

correspond to compounds of formula I wherein $R_o'$ is D—N=N— and p is 1 or $R_o'$ is —N=N—T—N=N— and p is 2, which compounds are metal-free monoazo, disazo, trisazo or polyazo compounds or 1:1 or 1:2 metal complexes thereof, which compounds or complexes form an essential part of this invention.

Preferably, in any disazo, trisazo or polyazo compound of formula IV containing a pyridone coupling component any N-substituent of this pyridine group is other than a group —$R_p$—NH—$R_{p1}$, wherein $R_p$ is linear or branched $C_{2-8}$-alkylene or 1,3- or 1,4-phenylene, and $R_{p1}$ is a group

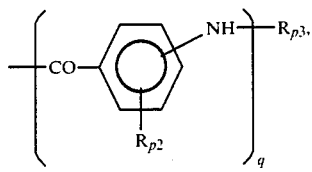

q is 0 or 1, $R_{p2}$ is hydrogen or a substituent and $R_{p3}$ is hydrogen or —CO(CH$_2$)$_{1\text{-}2}$R$_{p4}$, in which $R_{p4}$ is —NR$_{23}$R$_{24}$ or —NR$^{\oplus}_{25}$R$_{26}$R$_{27}$An$^{\ominus}$ and the groups $R_{23}$ to $R_{27}$ are as defined below; or $R_{p3}$ is a substituted triazinyl group

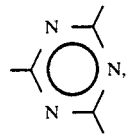

for example,

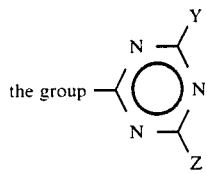

the group wherein Y and Z are as defined above.

Furthermore, it is preferred that for compounds of formula IV in which $R_o'$ is D—N=N— where D is the residue of a diazo component to form trisazo or polyazo compounds of formula IV those compounds containing any pyridone component together with a naphthol or hydroxynaphthylamine component are excluded.

Preferred azo compounds correspond to formula IVa

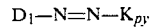

in which $K_{py}$ is as defined above, which are (ia) monoazo or disazo compounds in which $D_1$ is the radical of a diazo component of the carbocyclic- or heterocyclic-aromatic series;

(iia) trisazo or polyazo compounds in which $D_1$ is the radical of a diazo component of the formula

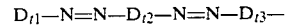

wherein $D_{t1}$ is the radical of a diazo component of the carbocyclic- or heterocyclic-aromatic series, each of $D_{t2}$ and $D_{t3}$, independently, is the radical of a coupling/diazo-component of the carbocyclic aromatic series;

(iiia) disazo or polyazo compounds in which $D_1$ is a group of the formula

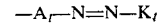

wherein $A_t$ is the radical of a tetrazo component, and $K_t$ is the radical of a coupling component of the aniline-, phenol-, naphthol-, aminonaphthalene-, aminonaphthol, acetoacetylalkyl- or -arylamide-, barbituric acid-, dimedone-, 2,6-diamino- or 2,4,6-triaminopyrimidine-, pyrazol-5-one- or 5-aminopyrazole-, where the nitrogen atom in position 1 of the pyrazole ring is unsubstituted or substituted by an alkyl or aryl group, quinolin-one- or isoquinolin-one series; a group of formula VIII defined below or the group $K_{py}$ defined above.

Where $K_t$ is a pyridone group of formula VIII this group, in one of the possible tautomeric forms, corresponds to the formula

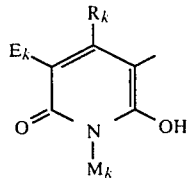

in which $R_k$ is hydrogen; $C_{1\text{-}4}$alkyl; —CH$_2$SO$_3$H; $C_{5\text{-}6}$cycloalkyl; phenyl, benzyl or phenylethyl, the phenyl group of the latter three substituents being unsubstituted or substituted by one or two groups selected from methyl, ethyl, methoxy, ethoxy and chlorine; $C_{1\text{-}4}$alkylamino or benzthiazolyl-2, $E_k$ is hydrogen, —CN, —COOR$_{15}$, —CONR$_{16}$R$_{17}$, —SO$_3$H, —CH$_2$R$_{18}$,

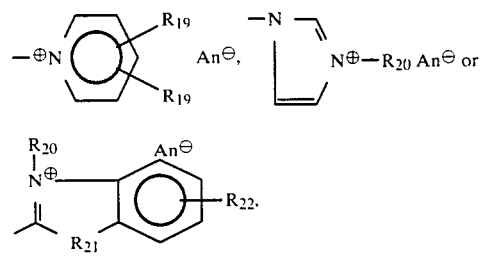

$R_{15}$ is $C_{1\text{-}6}$alkyl or phenyl-($C_{1\text{-}3}$alkyl), each of $R_{16}$ and $R_{17}$ is independently hydrogen or $C_{1\text{-}4}$alkyl, $R_{18}$ is —SO$_3$H or —NR$_{16}$R$_{17}$, each $R_{19}$ is independently hydrogen, $C_{1\text{-}4}$alkyl, —NR$_{16}$R$_{17}$ or —CONR$_{16}$R$_{17}$, $R_{20}$ is $C_{1\text{-}4}$alkyl, $R_{21}$ is —S—, —O— or

$R_{22}$ is hydrogen or $C_{1\text{-}4}$alkyl,

An$^{\ominus}$ is a non-chromophoric anion, $M_k$ is hydrogen; —NR$_{23}$R$_{24}$; $C_{1\text{-}6}$alkyl; hydroxy-C$_{2\text{-}4}$alkyl; $C_{1\text{-}4}$alkoxy-C$_{1\text{-}4}$alkyl; HO$_3$S—C$_{1\text{-}4}$alkyl; $C_{5\text{-}6}$cycloalkyl unsubstituted or substituted by one to three $C_{1\text{-}4}$alkyl groups; phenyl or phenyl($C_{1\text{-}3}$alkyl), the phenyl group of the latter two substituents being unsubstituted or substituted by one to three groups selected from $C_{1\text{-}4}$alkyl, $C_{1\text{-}4}$alkoxy and halogen; —V$_1$—NR$_{25}$R$_{26}$ or —V$_2$—N$^{\oplus}$R$_{25}$R$_{26}$R$_{27}$ An$^{\ominus}$;

each of $R_{23}$ and $R_{24}$ is independently hydrogen, $C_{1\text{-}6}$alkyl, $C_{2\text{-}6}$alkyl monosubstituted by hydroxy, cyano or halogen; phenyl or phenyl-($C_{1\text{-}3}$alkyl), the phenyl ring of the two latter substituents being unsubstituted or substituted by one to three groups selected from chlorine, $C_{1\text{-}4}$alkyl and $C_{1\text{-}4}$alkoxy; $C_{5\text{-}6}$cycloalkyl unsubstituted or substituted by one to three C$_{1-4}$alkyl groups, or R$_{23}$ and R$_{24}$, together with the nitrogen atom to which they are attached, form a 5- or 6-membered saturated ring which contains one to three hetero atoms and which may be further substituted by one to three C$_{1-4}$alkyl groups, each of R$_{25}$ and R$_{26}$ has independently one of the non-cyclic or cyclic significances of R$_{23}$ and R$_{24}$ provided that in the group —V$_1$—NR$_{25}$R$_{26}$ at least one of R$_{25}$ and R$_{26}$ is other than hydrogen, R$_{27}$ is C$_{1-4}$alkyl or phenyl-(C$_{1-3}$alkyl), and R$_{25}$, R$_{26}$ and R$_{27}$, together with the nitrogen atom to which they are attached, form a pyridine ring or a partially unsaturated 5- or 6-membered ring which contains one to three hetero atoms, where the pyridine ring and the partially unsaturated hetero ring are further unsubstituted or may be substituted by one to three C$_{1-4}$alkyl groups, V$_1$ is C$_{1-6}$alkylene or C$_{2-6}$alkenylene, and V$_2$ is C$_{2-6}$alkylene or C$_{2-6}$alkenylene.

The compounds of formula IVa are metal-free or are in 1:1 or 1:2 metal complex form, the complexing metal preferably being copper, iron, nickel, chromium or cobalt. Particularly preferred are the 1:1 copper complexes.

K$_{py}$ is preferably K$_{pya}$ where K$_{pya}$ is a group of formula IXa

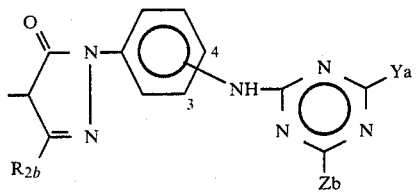
(IXa)

in which the —NH— group is bound to the 3- or 4-position. More preferred, it is K$_{pyb}$ where K$_{pyb}$ is a group of formula IXb which is a group of formula IXa in which R$_{2b}$ is methyl, Ya is Yb and Zb is Zc. Most preferred, it is K$_{pyc}$ where K$_{pyc}$ is a group of formula IXc which is a group of formula IXa in which R$_{2b}$ is methyl and each of Ya and Zb is Zd where both Zd groups are identical.

Preferably, in compounds of formula IVa of sections (ia) to (iiia) containing a group of formula II as defined for Y, R is hydrogen.

For compounds of formula IVa of section (ia) D$_1$ is preferably the radical of a diazo component of the aminobenzene-, aminonaphthalene-, aminophenyl-benzothiazole, aminophenyl-benzo, aminophenyl-benzoxazole-, aminophenyl-benzotriazole, aminoazobenzene- and aminobenzene-azo-naphthalene-series. More preferably, D$_1$ is the radical of a diazo component of the aminobenzene-, aminonaphthalene-, aminophenyl-benzthiazole-, aminoazobenzene- and aminobenzene-azo-naphthalene-series.

Preferably, D$_1$ of the compounds of section (ia) is D$_{1a}$, where D$_{1a}$ is a group of the formula

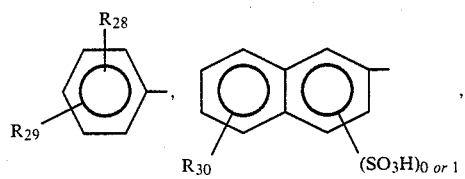

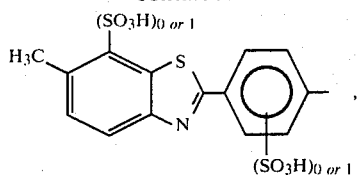

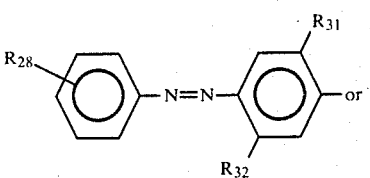

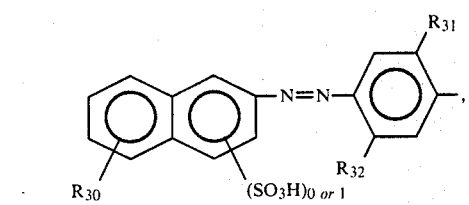

in which

R$_{28}$ is hydrogen, C$_{1-2}$alkyl, C$_{1-2}$alkoxy, acetamido, COOH, —SO$_3$H, —N$^\oplus$(CH$_3$)$_3$An$^\ominus$ or —CH$_2$N$^\oplus$(CH$_3$)$_3$An$^\ominus$, R$_{29}$ is hydrogen or C$_{1-2}$alkyl, R$_{30}$ is —SO$_3$H, —SO$_2$NH$_2$, —CH$_2$NH$_2$ or —CH$_2$N$^\oplus$(CH$_3$)$_3$An$^\ominus$, R$_{31}$ is hydrogen, C$_{1-2}$alkyl or C$_{1-2}$alkoxy, and R$_{32}$ is hydrogen, C$_{1-2}$alkyl, C$_{1-2}$alkoxy, —NHCOCH$_3$, —NHCONH$_2$ or —NHCOCH$_2$N$^\oplus$(CH$_3$)$_3$An$^\ominus$.

In compounds of formula IVa of section (iia) D$_{t1}$ is preferably D$_{t1a}$ where D$_{t1a}$ has one of the significances of D$_{1a}$. D$_{t2}$ and D$_{t3}$ are preferably D$_{t2a}$ and D$_{t3a}$ where each of D$_{t2a}$ and D$_{t3a}$ is independently a 1,4-phenylene group which is unsubstituted, monosubstituted by methyl, methoxy, —NHCOCH$_3$, —NHCONH$_2$ or —NHCOCH$_2$N$^\oplus$(CH$_3$)$_3$ An$^\ominus$, or disubstituted by methyl and/or methoxy.

In compounds of formula IVa of section (iiia) —A$_t$— as a radical of a tetrazo component is preferably derived from a diamine of the 1,3- or 1,4-phenylene or 1,5-naphthylene series or from a diamine of the formula

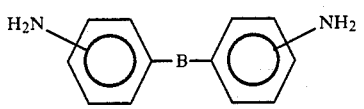

wherein each of the two amino groups is in m- or p-position to the carbon atom attached to B, each of the phenyl rings may be further substituted by one or two groups selected from halogen, cyano, C$_{1-4}$alkyl, C$_{1-4}$alkoxy, carboxy and sulpho; B is a direct bond or any divalent bridging group.

The group —A$_t$— is preferably —A$_{ta}$— of the formula

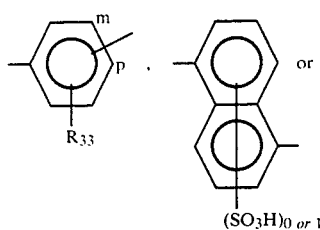

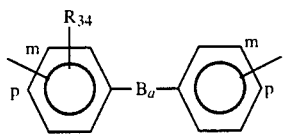

in which
R$_{33}$ is hydrogen, halogen, C$_{1-4}$alkyl, C$_{1-4}$alkoxy, cyano,
—CONH$_2$, —NHCOC$_{1-4}$alkyl, —NHCONH$_2$, —COOH or —SO$_3$H,
each R$_{34}$ is independently hydrogen, halogen, cyano, C$_{1-4}$alkyl, C$_{1-4}$alkoxy, COOH or SO$_3$H, and
B$_a$ is a direct bond, —O—, —S—, —NH—, ${+}$CH$_2{)}_{\overline{1-3}}$, —NHCO—, —NHCONH—, —CH=CH—, —N=N—, —N=N—$\overset{O}{\uparrow}$, —CO—, —O${+}$CH$_2{)}_{\overline{2-3}}$O—, —CONH(CH$_2$)$_{2-3}$NHCO—,

—NHCO(CH$_2$)$_{2-3}$CONH—, —NHCOCH=CH—CONH—,

—NHCOCH$_2\overset{\oplus}{N}$(CH$_3$)$_2{+}$CH$_2{)}_{\overline{2-3}}\overset{\oplus}{N}$(CH$_3$)$_2$CH$_2$CONH—,

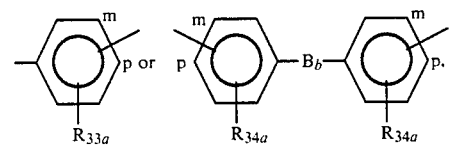

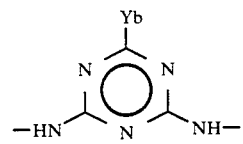

and each phenylene group is linked through the m- or p-position.

More preferably, —A$_t$— is —A$_{tb}$— where —A$_{tb}$— is a group of the formula

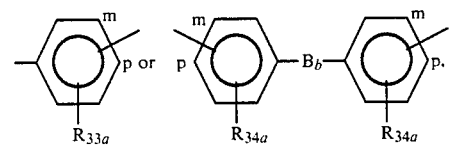

in which
R$_{33a}$ is hydrogen, C$_{1-2}$alkyl, C$_{1-2}$alkoxy or —NHCOCH$_3$,
R$_{34a}$ is independently hydrogen, chlorine, methyl, methoxy or —SO$_3$H, and
B$_b$ is ${+}$CH$_2{)}_{\overline{1-3}}$, —NHCONH—, —CONH— or -continued

and each phenylene group is linked through the m- or p-position.
K$_t$ is preferably a group of formula VIII or (IXa) or is the radical of a coupling component of the naphthol-, acetoacetarylamide-, pyrazole- or barbituric acid-series.

Preferably, K$_t$ is K$_{ta}$ where K$_{ta}$ is a group of formula VIII or IXc or a group of the formulae

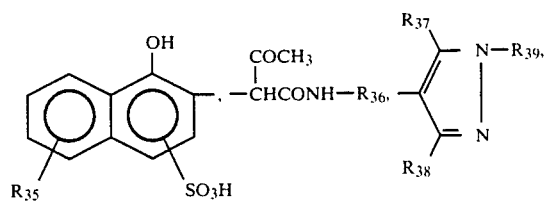

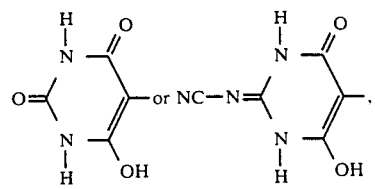

in which
R$_{35}$ is hydrogen or —NHCOCH$_3$,
R$_{36}$ is

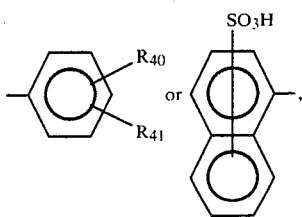

$R_{40}$ is hydrogen or methoxy,
$R_{41}$ is hydrogen, —CH$_2$N$^\oplus$(CH$_3$)$_3$ An$^\ominus$, —CONH—Q$_{3c}$—NR$_{8b}$R$_{9b}$, —SO$_2$NH—Q$_{3c}$—NR$_{8b}$R$_{9b}$ or

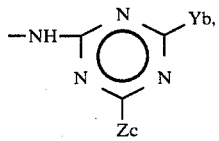

$R_{37}$ is —OH or —NH$_2$,
$R_{38}$ is —CH$_3$, —C$_6$H$_5$, —COOH, —CH$_2$COOH or —COOCH$_3$,.
$R_{39}$ is hydrogen, —CH$_2$CH=CH$_2$,

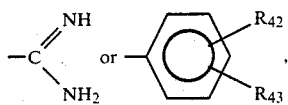

$R_{42}$ is hydrogen, halogen, C$_{1-2}$alkyl, C$_{1-2}$alkoxy, —SO$_3$H, —NHCOCH$_2$N$^\oplus$(CH$_3$)$_3$ An$^\oplus$, —N$^\oplus$(CH$_3$)$_3$ An$^\ominus$, —CH$_2$N$^\oplus$(CH$_3$)$_3$ An$^\ominus$ or —CH$_2$NR$_{8b}$R$_{9b}$, and
$R_{43}$ is hydrogen or halogen.

Most preferred are azo compounds which correspond to the following formulae:
(ib) compounds of formula IVb (i);

      IVb (i)

$D_{1a}$—N=N—$K_{pya}$ (iib) compounds of formula IVb (ii);

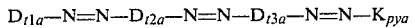      IVb (ii)

$D_{t1a}$—N=N—$D_{t2a}$—N=N—$D_{t3a}$—N=N—$K_{pya}$ and
(iiib) compounds of formula IVb (iii),

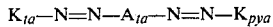      IVb (iii)

$K_{ta}$—N=N—$A_{ta}$—N=N—$K_{pya}$ in which —$A_{ta}$— particularly is —$A_{tb}$—.

Even more preferred are compounds of sections (ib) to (iiib) in which $K_{pya}$ is $K_{pyb}$, especially $K_{pyc}$.

All diazo and coupling components indicated above may contain metallizable groups such as —OH, —OCH$_3$, —NH$_2$ or —COOH, each of which is bound to a carbon atom in an ortho position to the azo group.

Preferred metallizable groups are hydroxy and methoxy groups. Any conventionally used metals are suitable as 1:1 or 1:2 metal complex-forming metal. Particularly preferred are 1:1 copper complexes in which the metal is bound via oxygen bridges.

Any sulpho and carboxy groups present in the compounds of formula IV may react with basic or cationic groups, e.g., with a group Z to form an internal salt of the type (Z—H)$^\oplus$SO$_3^\ominus$/COO$^\ominus$ or Z$^\oplus$SO$_3^\ominus$/COO$^\ominus$. Any additional basic or cationic groups may form external salts (with suitable acids) or are already in salt form. Suitable anions or acids are as indicated above.

Compounds of formula IV which are compounds of formula I wherein R$_o$ is other than hydrogen may be prepared by reacting a diazotized amino compound of formula Va or Vb D—NH$_2$      Va H$_2$N—T—H$_2$      Vb with a compound of formula VI K$_{py}$—H      VI using the corresponding stoichiometric molar ratio to obtain a compound of formula IV as defined above and optionally converting the obtained metal-free compound of formula IV into the corresponding 1:1 or 1:2 metal complex.

Diazotization and coupling reactions may be effected in conventional manner. Advantageously, coupling is carried out in aqueous medium at a temperature from 0° to 50° C., preferably from 0° to 30° C., and at a pH range of 2 to 9, preferably at pH 3 to 6.

Compounds of formula IV containing metallizable groups ortho to the azo group may be converted into metal complexes by reacting with the metal-free compound of formula IV a metal-donating compound which is employed in such an amount to provide at least one equivalent of metal per equivalent of monoazo compound to be metallized.

The preferred 1:1 metallization is carried out in accordance with known methods. Suitably, the preferred 1:1 copper complexes are prepared either by oxidative coppering, preferably at 40°–70° C. and at pH 4–7 in the presence of copper(II) salts or using copper powder in the presence of hydrogen peroxide or other conventional oxidizing agents; or preferably by demethylation coppering, preferably at pH 3–4 and at elevated to boiling temperature in the presence of copper(II) salts.

The compounds of formula IV may be isolated in accordance with known methods.

Those compounds of formula IV containing basic groups may be converted into water-soluble salts by reacting with at least stoichiometric amounts of an inorganic mineral acid such as hydrochloric acid, sulphuric acid, phosphoric acid or preferably an organic acid such as formic acid, acetic acid, lactic acid, citric acid, glycolic acid and methanesulphonic acid.

The starting materials of formulae Va and Vb are either known or may be prepared in accordance with known methods from available starting materials.

The compounds of formula I, in water-soluble salt form, acid addition salt form or quaternary ammonium salt form, are dyestuffs and are useful for dyeing cationic dyeable materials such as homo or mixed polymers of acrylonitrile, acid modified polyester, polyamide e.g. wool, leather, cotton, bast fibres such as hemp, flax, sisal, jute, coir and straw, regenerated cellulose fibres, glass fibres and paper.

Preferably, the dyestuffs according to the invention are used for dyeing and printing fibres, filaments and textiles consisting of or containing cellulose, e.g. cotton, in accordance with known methods. Cotton is preferably dyed by the conventional exhaust method from a long or short liquor using temperatures from room to boiling temperature. Printing may be effected by impregnation with a printing paste produced by known methods.

The new dyestuffs are also well suited for dyeing and printing leather, including low affinity vegetable-tanned leather, in accordance with known methods. Furthermore, the dyestuffs may be used for dyeing glass fibres.

Most preferably, the dyestuffs according to the invention are used for dyeing and printing paper e.g., for the preparation of sized or unsized, wood-free or ligneous paper. They may be used for the production of pulp-coloured paper or of paper dyed in the size press. Similarly, the dyestuffs may be used for dyeing paper by the dipping process. The dyeing and printing of paper is effected by known methods.

The dyeings and prints and particularly those obtained on paper show good fastness properties.

The compounds of formula I may be converted into dyeing preparations. Processing into stable liquid, preferably aqueous, or solid dyeing preparations may take place in a generally known manner. Advantageously, suitable liquid preparations may be made by dissolving the dyestuff in suitable solvents such as mineral acids, or organic acids e.g., hydrochloric acid, sulphuric acid, phosphoric acid, formic acid, acetic acid, lactic acid, glycolic acid, citric acid and methanesulphonic acid, formamide, dimethylformamide, urea, glycol, diglycol, diglycol ether and glycerin, which may be used together with water, optionally adding an assistant e.g., a stabilizer. Such preparations may be obtained, for example, as described in French Patent Specification No. 1,572,030.

An example of a suitable liquid dye preparation is (all parts are by weight):
100 parts of a compound of formula I in salt form, acid addition salt form or in quaternary ammonium salt form
1–100 parts, preferably 1–10 parts, of an inorganic salt
1–100 parts of an organic acid such as formic, acetic, lactic and citric acids.
100–800 parts water
0–500 parts of a solubilizing agent (e.g., glycols such as diethylene glycol, triethylene glycol and hexylene glycol; glycol ethers such as Methyl Cellosolve ®, Methyl Carbitol ®, butylpolyglycol; urea; formamide and dimethylformamide).

Advantageously, solid dyeing preparations may be made by grinding or, preferably, granulating, for example, in accordance with the method described in French Patent Specification No. 1,581,900.

A suitable granulate preparation comprises (all parts are by weight):
100 parts of a compound of formula I in salt form, acid addition salt form or quaternary ammonium salt form
1–100 parts, preferably 1–10 parts, of an inorganic salt
0–800 parts of a standardizing agent (preferably non-ionic such as dextrin, sugar, glucose and urea).

The solid preparations may contain up to 10% residual moisture.

The dyestuffs of formula I (in salt form) have good solubility, especially in cold water. Owing to their good substantivity the dyestuffs exhaust practically quantitatively and show good build-up power. When producing sized or unsized paper the waste water is essentially colourless. The dyestuffs can be added to the stock as a dry powder or granulate and can also be used in soft water without loss of yield. They do not mottle applied on paper and are practically insensitive to filler or pH variations.

The paper dyeings made with the dyestuffs according to the invention are clear and brilliant and have good light fastness; on exposure to light for a long time the shade of the dyeing fades tone in tone. The dyeings on paper show high wet fastness properties not only for water but also for milk, fruit juice, sweetened mineral water, soap and sodium chloride solution. Furthermore, the paper dyeings have good alcohol fastness.

Paper dyed with the new dyestuffs can be bleached oxidatively or reductively which is important for the recycling of waste and old paper.

The dyestuffs may also be used to dye paper with wood-pulp where even dyeings having good fastness properties are obtained. Furthermore, the dyestuffs may be used for the production of coated paper in accordance with known manner. Preferably, a suitable filler, for example kaolin, which due to its tendency for pigmentation is dyed with the dyestuff according to the invention, is employed to give a one side coated paper.

The new dyestuffs are also suitable for dyeing in combination. The thus obtained dyeings have good fastness properties.

The following Examples further serve to illustrate the invention. In the Examples all parts and percentages are by weight or volume, and the temperatures given are in degrees Centigrade, unless indicated to the contrary.

EXAMPLE 1a

91 Parts of cyanuric chloride are suspended in 240 parts ice water and 133 parts of 3-N,N-diethylaminopropylamine are added dropwise at 5°–10°. After stirring for three hours 75 parts of 4'-amino-3-methyl-1-phenyl-5-pyrazolone are added. The temperature is elevated to 90° and the pH is kept at 2–3 by the addition of sodium acetate. A solution is obtained containing the coupling component of the formula

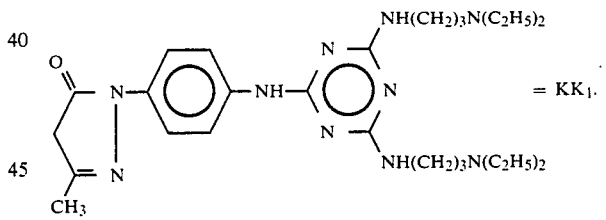

This solution can be used directly, without isolating the compound, as a coupling component in the preparation of azo dyestuffs.

EXAMPLES 1b TO 1h

According to the method described in Example 1a further coupling components may be prepared by using the corresponding amount of an analogous compound instead of 75 parts of the above pyrazolone compound. The resulting compounds correspond to the formula

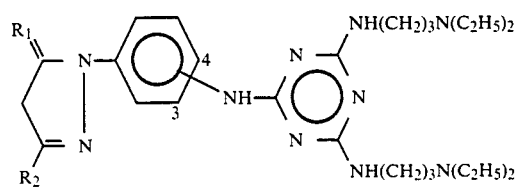

and are listed in the following Table 1.

TABLE 1

| Ex. No. | $R_1$ | $R_2$ | position in phenyl ring | |
|---|---|---|---|---|
| 1b | O | $CH_3$ | 3 | $= KK_2$ |
| 1c | O | COOH | 4 | $= KK_3$ |
| 1d | O | $COOCH_3$ | 4 | |
| 1e | NH | $CH_3$ | 4 | $= KK_4$ |
| 1f | O | COOH | 3 | |
| 1g | NH | $CH_3$ | 3 | $= KK_5$ |
| 1h | O | $CONH_2$ | 4 | |

The compounds of Examples 1b to 1h are obtained in solution; they can be used directly in the preparation of azo dyestuffs.

EXAMPLE 1i

In a similar manner to the method of Example 1a but using the compound of formula

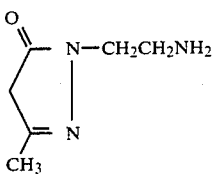

as starting material, a solution of the coupling component of the formula

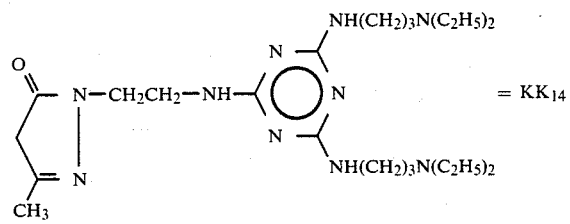

is obtained which can be used directly without further isolation.

EXAMPLE 2

22 Parts of the compound of the formula

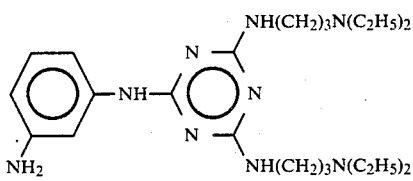

are dissolved in 140 parts water and 20 parts 30% hydrochloric acid and cooled to 0°. 13 Parts 4N sodium nitrite solution are added and diazotization is effected in conventional manner. Subsequently, 9.7 parts of acetylsuccinic acid dimethyl ester are added. At pH 6 adjusted by the addition of sodium carbonate the coupling to a yellow dye solution takes place. Then 7 parts 30% sodium hydroxide solution are added. The mixture is warmed to 70°, the resulting solution is practically colourless. To discolour the solution completely 10 parts of sodium dithionite 85% are added and stirring is effected for a further hour at 90°. After cooling, a solution containing the coupling component of the formula

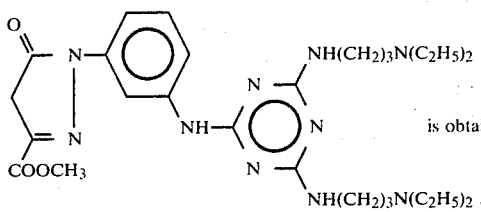

is obtained.

EXAMPLE 3

To an aqueous suspension of 92 parts cyanuric chloride 119 parts of 4'-amino-1-phenyl-5-pyrazolone-3-carboxylic acid ethylester are added and are reacted at 0°–5° and at pH 4–5. The thus obtained condensation product filtered by suction and thoroughly pressed is added to 500 parts of 3-N,N-dimethylaminopropylamine. The temperature of the resulting viscous mass rises to 70° and is elevated to 95°–100°. Stirring is effected at this temperature for 16 hours. After cooling to room temperature, 400 parts water are added, and the oil which precipitates is separated and stirred into a mixture of water and acetic acid until the solution containing a coupling component of the formula

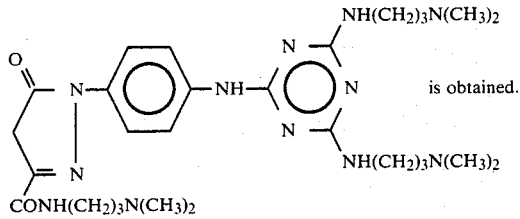

is obtained.

EXAMPLE 4

44 Parts of the compound of the formula

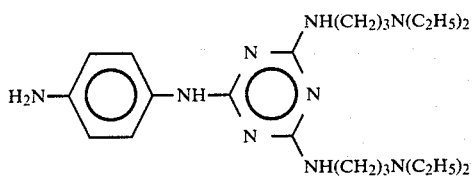

are dissolved in 200 parts water and 20 parts 30% hydrochloric acid. To the solution 100 parts ice are added and diazotization is carried out in conventional manner in the presence of 7 parts 4N sodium nitrite. After the addition of 60 parts 40% bisulphite solution the mixture is stirred for one hour at 30°. When a diazo compound is no longer detectable 50 parts 30% hydrochloric acid are added.

The reaction mixture is heated to 95° and kept at this temperature until the amount of sulphur dioxide has evaporated quantitatively. Subsequently, 10 parts of 3-aminocrotononitrile are added at pH 1. The temperature rises to 40° and is kept during one hour. The resulting solution contains a coupling component of the formula

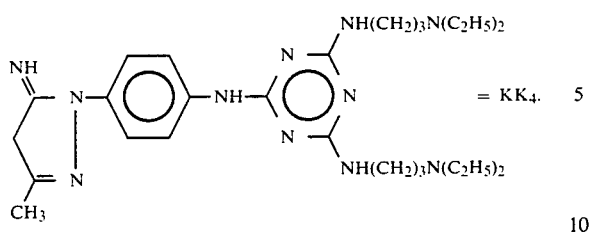 = KK₄.

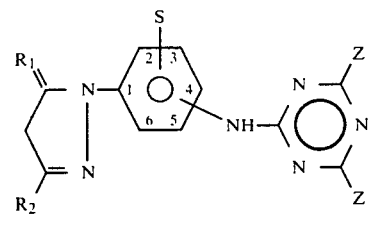

and are listed in the following Table 2.

TABLE 2

| Ex. No. | R₁ | R₂ | position of —NH—triazine | S (position) | Z | |
|---|---|---|---|---|---|---|
| 5a | O | CH₃ | 4 | H | —NH(CH₂)₃N(CH₃)₂ | = KK₆ |
| 5b | O | CH₃ | 3 | H | " | = KK₇ |
| 5c | NH | CH₃ | 4 | H | " | |
| 5d | NH | CH₃ | 3 | H | " | |
| 5e | O | CH₃ | 4 | SO₃H (2) | " | |
| 5f | O | COOCH₃ | 3 | H | " | |
| 5g | O | COOCH₃ | 4 | H | " | |
| 5h | O | CH₃ | 3 | H | —NH(CH₂)₂N(C₂H₅)₂ | = KK₈ |
| 5i | O | CH₃ | 4 | H | " | = KK₉ |
| 5j | O | CONH₂ | 3 | H | " | |
| 5k | O | CH₃ | 4 | H | —N⟨piperazine⟩N—C₂H₄NH₂ | = KK₁₀ |
| 5l | O | CH₃ | 3 | H | " | |
| 5m | O | CH₃ | 4 | SO₃H (2) | " | |
| 5n | O | CH₃ | 3 | H | —NHNHCOCH₂N⁺(CH₃)₃Cl⁻ | = KK₁₁ |
| 5o | O | CH₃ | 4 | H | " | |
| 5p | O | CH₃ | 4 | H | —NH—C₆H₄—N⁺(CH₃)₃Cl⁻ | = KK₁₂ |
| 5q | O | CH₃ | 3 | H | —NH(CH₂)₂N(CH₃)₂ | |
| 5r | O | CH₃ | 4 | H | " | |
| 5s | O | CO—Z | 3 | H | —NH(CH₂)₃N(C₂H₅)₂ | = KK₁₃ |
| 5t | O | " | 4 | H | " | |

EXAMPLES 5a TO 5t

According to the method described in Examples 1 to 4 further coupling components may be obtained which correspond to the formula

EXAMPLE 6

2.4 Parts of 2-(4'-aminophenyl)-6-methylbenzthiazole (component I) is diazotized at 0°–5° in the presence of hydrochloric acid in conventional manner and is then coupled to 6 parts of the coupling component of Example 1a at pH 4–5 in the presence of sodium acetate. From the obtained dark yellow solution the dyestuff is precipitated by the addition of sodium hydroxide solution and is filtered and dried. The thus obtained dyestuff corresponding to the formula

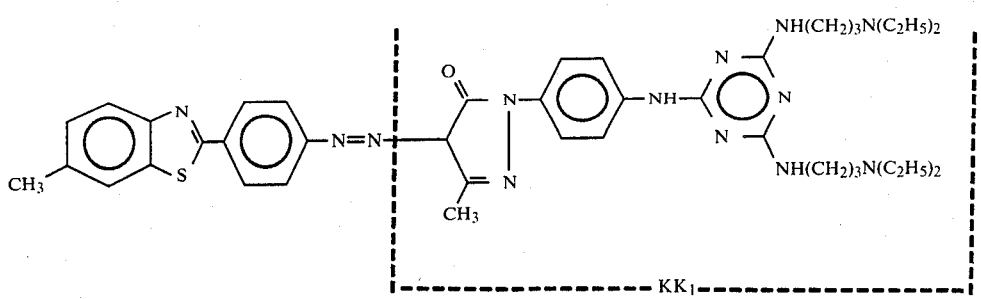
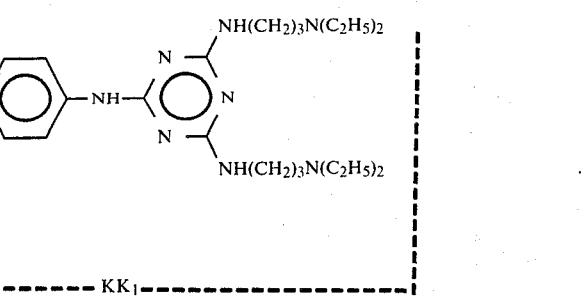

is a yellow powder; the dyestuff, in acid addition salt form, dyes paper in clear yellow shades.

EXAMPLE 7

In a similar manner to the method of Example 6 a compound which, in the free acid form, corresponds to the formula

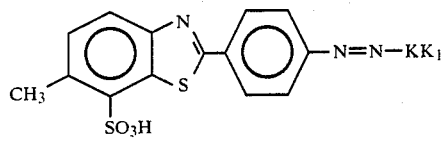

may be obtained using 3.2 parts 2-(4'-aminophenyl)-6-methylbenzthiazole-7-sulphonic acid instead of 2.4 parts of component I. The dyestuff (in form of an acid addition salt) dyes paper a yellow tone.

EXAMPLE 8

When 4 parts of 2-(4'-aminophenyl)-6-methylbenzthiazole-3',7-disulphonic acid are used instead of 2.4 parts of component I, and the reaction is carried out according to the method described in Example 6, a dyestuff of the formula (defined in the free acid form)

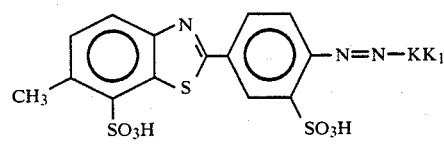

is obtained which dyes paper a yellow tone.

EXAMPLE 9

When 2 parts 4-amino-1,1'-azobenzene are used in Example 6 instead of the component I a dyestuff corresponding to the formula

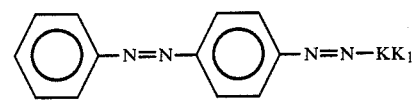

is obtained which in form of an acid addition salt dyes paper a yellow shade.

EXAMPLE 10

When in Example 6 a hydrochloric acid solution containing 2.5 parts 2-aminonaphthalene-5-methyl-trimethylammonium chloride is used instead of the component I a dyestuff of the formula

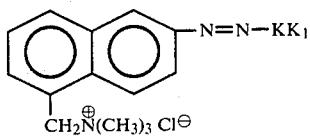

is prepared which, in weakly acid solution, dyes paper a golden-yellow tone.

EXAMPLE 11

When in Example 9 4.7 parts of a compound of the formula

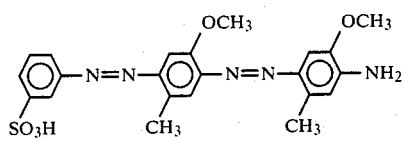

are used instead of 4-amino-1,1'-azobenzene the dyestuff of the formula

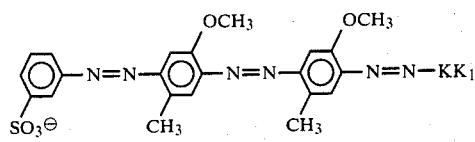

is obtained which in form of an acid addition salt dyes paper a brown tone.

EXAMPLE 12

When according to the method of Example 11 4.2 parts of the compound of the formula

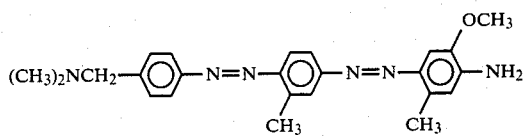

are used the corresponding dyestuff is obtained which dyes paper a brown shade.

EXAMPLE 13

When using 2 parts 2-aminonaphthalene-6-sulphonic acid instead of component I according to the method give in Example 6 a dyestuff corresponding to the formula

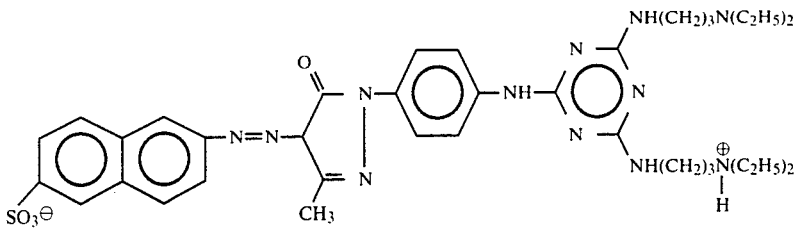

is obtained which in the acid addition salt form dyes paper a reddish-yellow tone.

EXAMPLE 14

When instead of the coupling component KK$_1$ according to the method of Example 9 6 parts of the coupling component of with Example 1b are used the dyestuff of the formula

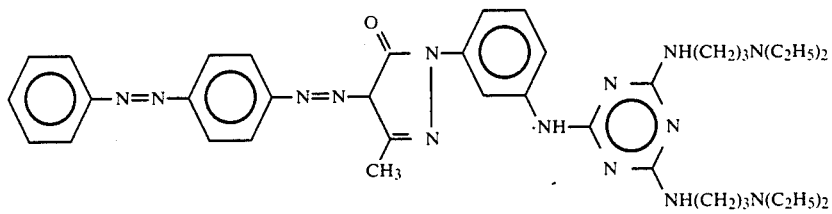

is obtained which (in acid addition salt form) dyes paper a yellow tone.

EXAMPLE 15

2 Parts of 4,4'-diaminodiphenylmethane are diazotized with respect to both amino groups at 0°–5° in diluted hydrochloric acid solution according to a conventional manner and are coupled with 12.5 parts of the coupling component of Example 1a. After one hour the coupling which is effected at pH 6 to 6.5 in the presence of sodium carbonate is completed. A dark reddish-yellow solution containing the dyestuff is obtained; it is precipitated, filtered by suction and then dried. It corresponds to the formula

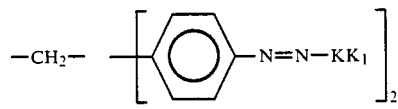

The dyestuff in form of an acid addition salt dyes paper a neutral-yellow tone. The resulting paper dyeings show good light and wet fastness properties.

EXAMPLES 16 TO 59

By a method in accordance with Example 15 further dyes may be prepared which are listed in the following Table 3. These dyestuffs correspond to the general formula

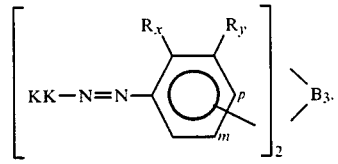

In the last column of Table 3 the dye shade on paper is given whereby a=yellow; b=yellowish-orange; c=orange; d=brown-orange and e=brown.

The coupling components KK are defined as given for Examples 1 to 5.

The obtained paper dyeings show good light and wet fastness properties.

TABLE 3

| Ex. No. | KK | —B$_3$— (position) | R$_x$ | R$_y$ | shade on paper |
|---|---|---|---|---|---|
| 16 | KK$_1$ | —O— (p) | H | H | a |
| 17 | KK$_2$ | " | H | H | a |
| 18 | KK$_2$ | —CH$_2$— (p) | H | H | a |
| 19 | KK$_4$ | " | H | H | a |
| 20 | KK$_9$ | " | H | H | a |
| 21 | KK$_1$ | —C$_2$H$_4$— (p) | H | H | a |
| 22 | KK$_2$ | " | H | H | a |
| 23 | KK$_6$ | " | H | H | a |
| 24 | KK$_1$ | —NHCO— (p) | H | H | a |
| 25 | KK$_2$ | " | H | H | a |
| 26 | KK$_3$ | " | H | H | a |
| 27 | KK$_4$ | " | H | H | a |
| 28 | KK$_6$ | " | H | H | a |
| 29 | KK$_{10}$ | " | H | H | a |
| 30 | KK$_{11}$ | " | H | H | a |
| 31 | KK$_{12}$ | " | H | H | a |
| 32 | KK$_{13}$ | " | H | H | a |
| 33 | KK$_1$ | —NHCO— (m) | H | H | a |

TABLE 3-continued

| Ex. No. | KK | —B₃— (position) | $R_x$ | $R_y$ | shade on paper |
|---|---|---|---|---|---|
| 34 | KK₉ | " | H | H | a |
| 35 | KK₁ | —NHCONH— (p) | H | H | c |
| 36 | KK₂ | " | H | H | b |
| 37 | KK₁₀ | " | H | H | c |
| 38 | KK₇ | " | H | H | b |
| 39 | KK₅ | " | H | H | b |
| 40 | KK₁ | —NHCONH— (m) | H | H | a |
| 41 | KK₂ | " | H | H | a |
| 42 | KK₈ | " | H | H | a |
| 43 | KK₁ | —N=N— (p) (with O↑) | H | H | d |
| 44 | KK₁ | —N=N— (p) | $OCH_3$ | H | d |
| 45 | KK₁ | —NHCONH— (p) | $OCH_3$ | H | c |
| 46 | KK₆ | " | $OCH_3$ | H | c |
| 47 | KK₁ | —CH=CH— (p) | H | H | c |
| 48 | KK₅ | " | H | H | c |
| 49 | KK₁ | " | H | $SO_3H$ | c |
| 50 | KK₂ | " | H | $SO_3H$ | c |
| 51 | KK₇ | " | H | $SO_3H$ | c |
| 52 | KK₁ | —NH— (p) | H | H | e |
| 53 | KK₁₄ | " | H | H | e |
| 54 | KK₁ | direct bond (p) | $OCH_3$ | H | c |
| 55 | KK₁ | triazine —HN-...-NH— (p), NHCH₂CH₂OH | H | H | c |
| 56 | KK₂ | " | H | H | c |
| 57 | KK₁ | triazine —HN-...-NH— (m), NH(CH₂)₃N(C₂H₅)₂ | H | H | b |
| 58 | KK₂ | " | H | H | b |
| 59 | KK₆ | triazine —HN-...-NH— (p), NH(CH₂)₃N(CH₃)₂ | H | H | b |

EXAMPLE 60

When using the tetrazo component of the formula

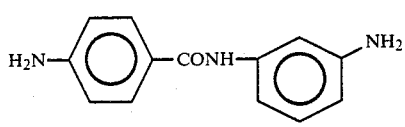

instead of 4,4′-diaminodiphenylmethane in accordance with the method of Example 15 the dyestuff of the formula

is obtained which (in an acid addition salt form) dyes paper a yellow tone.

EXAMPLE 61

When a tetrazo component of the formula

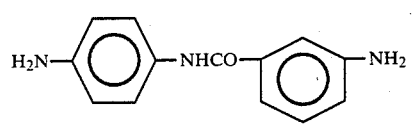

is used in accordance with the method of Example 60 the dyestuff having the formula

is obtained; it has dyeing properties similar to those of the dye of Example 60.

EXAMPLE 62

When using according to the method of Example 60 a compound of the formula

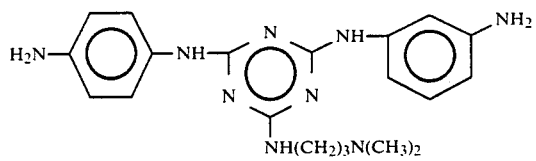

the dyestuff corresponding to the formula

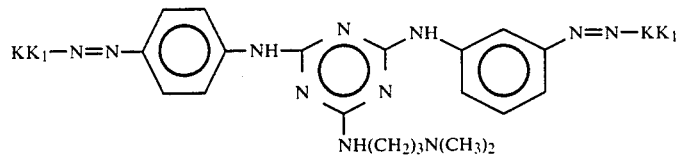

is obtained. The dyeing properties are similar to those of the dyes of Examples 60 and 61.

EXAMPLE 63

2.3 Parts of 4,4'-diaminobenzanilide are diazotized at 0°–5° in a conventional manner. A hydrochloric acid solution containing 6 parts of the coupling component of Example 1a is added. Within one hour the pH is gradually adjusted to 5 by the addition of sodium carbonate. When coupling on one side has been completed 2.4 parts of 6-hydroxy-4-methylpyridone-3-yl-pyridinium betaine are added. The pH is adjusted to 6.5. After two hours the second coupling is completed. The obtained dyestuff is salted out, filtered and dried. It corresponds to the formula

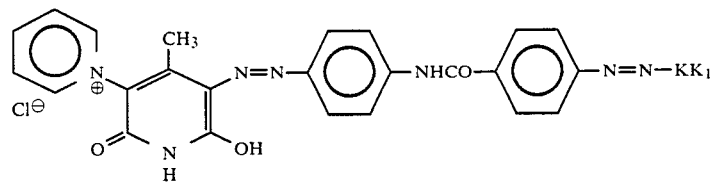

and is an orange powder. The dyestuff which is well soluble in organic acids such as acetic or lactic acid dyes paper in yellow-orange shades. The paper dyeings have good light and wet fastness properties.

EXAMPLE 64

When according to the method given in Example 63 the sequence of the coupling steps is changed, i.e. using for the first coupling the pyridone component and for the second one the coupling component of Example 1a, a dyestuff is obtained the structure of which is given in the following Table which dyes paper a yellow-orange shade. This paper dyeing is somewhat more yellow than that made with the dye of Example 63.

EXAMPLES 64 TO 151

According to the method described in Examples 63 and 64 further dyestuffs may be prepared which correspond to the general formula

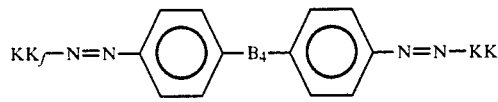

and are listed in the following Table 4. Any starred carbon or nitrogen atom in the definition of the bridging group —$B_4$— is bound to the phenyl group attached to the $KK_f$—N=N— group. The coupling components under the column KK are defined as given in Examples 1 to 5.

In the last column of Table 4 the shade of the obtained paper dyeings is given whereby a=yellow; b=yellow-orange; f=yellowish-red and g=rubine.
The paper dyeings made with the dyestuffs in Table 4 have good light and wet fastness properties.

TABLE 4

| Ex. No. | $KK_f$ | —$B_4$— | KK | shade on paper |
|---|---|---|---|---|
| 64 | (pyridinium-pyridone structure with CH₃, Cl⁻, OH, NH) | *—CONH— | $KK_1$ | b |
| 65 | " | *—NHCO— | $KK_2$ | b |
| 66 | " | " | $KK_6$ | b |

TABLE 4-continued

| Ex. No. | KK_f | —B_4— | KK | shade on paper |
|---|---|---|---|---|
| 67 | (3-methylpyridinium chloride substituted 4,6-dimethyl-2-oxo-6-hydroxy pyridine) | " | KK_1 | a |
| 68 | " | " | KK_7 | a |
| 69 | " | —*CONH— | KK_1 | a |
| 70 | (3-cyano-4,6-dimethyl-2-oxo-6-hydroxy pyridine) | " | KK_1 | a |
| 71 | " | —*NHCO— | KK_1 | a |
| 72 | (2-methoxyphenyl-NHCOCH(COCH_3)—) | " | KK_1 | a |
| 73 | " | " | KK_4 | a |
| 74 | " | —*CONH— | KK_1 | a |
| 75 | (5-methylbarbituric acid enol) | " | KK_1 | a |
| 76 | " | —*NHCO— | KK_1 | a |
| 77 | (pyridinium chloride substituted 4,6-dimethyl-2-oxo-6-hydroxy-1-(CH_2)_3N(CH_3)_2 pyridine) | —*CONH— | KK_1 | b |
| 78 | " | —*NHCO— | KK_1 | b |
| 79 | (3-sulfo-4,6-dimethyl-2-oxo-6-hydroxy-1-methyl pyridine) | " | KK_1 | b |
| 80 | " | —*CONH— | KK_1 | b |

TABLE 4-continued

| Ex. No. | KK$_f$ | —B$_4$— | KK | shade on paper |
|---|---|---|---|---|
| 81 | [structure: 4,5-dimethyl-3-(HO$_3$SCH$_2$)-1-methyl-6-hydroxy-2-pyridone] | " | KK$_1$ | b |
| 82 | [structure: 4,5-dimethyl-1-(CH$_2$CH$_2$SO$_3$H)-6-hydroxy-2-pyridone] | " | KK$_1$ | b |
| 83 | " | —*NHCO— | KK$_2$ | b |
| 84 | [structure: 4,5-dimethyl-3-(H$_2$NOC)-6-hydroxy-2-pyridone, NH] | " | KK$_1$ | b |
| 85 | " | —*CONH— | KK$_1$ | b |
| 86 | [structure: benzothiazolyl-pyridone with CH$_3$, OH] | " | KK$_1$ | b |
| 87 | " | —*NHCO— | KK$_1$ | b |
| 88 | [structure: pyridine with NHC$_2$H$_5$, CN, CH$_3$, NH$_2$, N-C$_2$H$_5$, HN=] | " | KK$_1$ | b |
| 89 | " | —*CONH— | KK$_2$ | b |
| 90 | [structure: 4,5-dimethyl-3-((CH$_3$)$_2$NH$_2$C)-1-ethyl-6-hydroxy-2-pyridone] | —*NHCO— | KK$_1$ | b |
| 91 | " | —*CONH— | KK$_6$ | b |

TABLE 4-continued
| Ex. No. | KK$_f$ | —B$_4$— | KK | shade on paper |
|---|---|---|---|---|
| 92 | 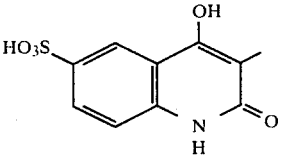 | " | KK$_1$ | b |
| 93 | " | —$\overset{*}{\text{N}}$HCO— | KK$_7$ | b |
| 94 | 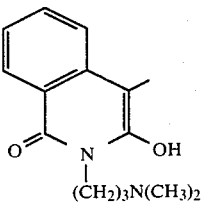 | " | KK$_1$ | b |
| 95 | " | —$\overset{*}{\text{C}}$ONH— | KK$_1$ | b |
| 96 | 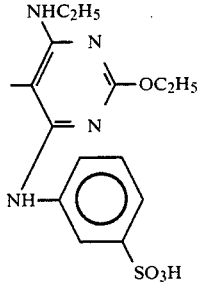 | " | KK$_1$ | b |
| 97 | " | —$\overset{*}{\text{N}}$HCO— | KK$_1$ | b |
| 98 | 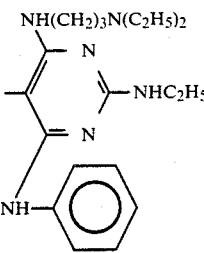 | " | KK$_1$ | b |
| 99 | 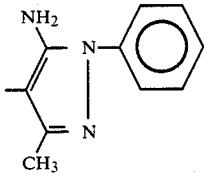 | " | KK$_1$ | b |
| 100 | " | —$\overset{*}{\text{C}}$ONH— | KK$_7$ | b |
| 101 | 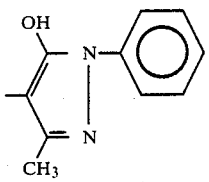 | " | KK$_1$ | b |
| 102 | " | —$\overset{*}{\text{N}}$HCO— | KK$_1$ | b |

TABLE 4-continued

| Ex. No. | KKf | —B4— | KK | shade on paper |
|---|---|---|---|---|
| 103 | (phenyl-N=N-pyrazole with NH2, CH3, and N-phenyl-SO3H substituents) | " | KK1 | b |
| 104 | (pyrazolone with OH, CH3, N-CH2CH=CH2) | " | KK1 | b |
| 105 | (pyrazolone with OH, CH3, N-phenyl, CH2COOH) | " | KK6 | b |
| 106 | (pyrazolone with OH, CH3, N-phenyl, COOH) | " | KK1 | b |
| 107 | (pyridone with CH3, CH3, OH, N-CH2CH2-phenyl-SO3H) | " | KK1 | b |
| 108 | " | *—CONH— | KK1 | b |
| 109 | (pyrazolone with OH, CH3, N-phenyl-SO3H, CH3) | " | KK1 | b |
| 110 | " | *—NHCO— | KK1 | b |
| 111 | (pyrazolone with HO, CH3, N—H, CH3) | " | KK1 | b |

TABLE 4-continued
| Ex. No. | KK$_f$ | —B$_4$— | KK | shade on paper |
|---|---|---|---|---|
| 112 | " | *—CONH— | KK$_1$ | b |
| 113 | 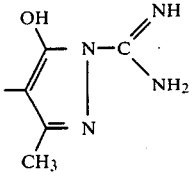 | " | KK$_1$ | b |
| 114 | " | *—NHCO— | KK$_2$ | b |
| 115 | 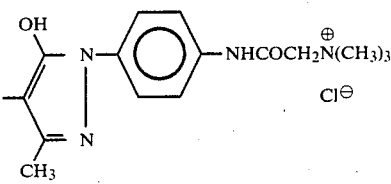 | " | KK$_1$ | b |
| 116 | " | *—CONH— | KK$_1$ | b |
| 117 | 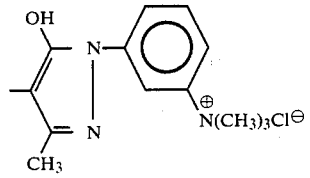 | " | KK$_1$ | b |
| 118 | " | *—NHCO— | KK$_1$ | b |
| 119 | 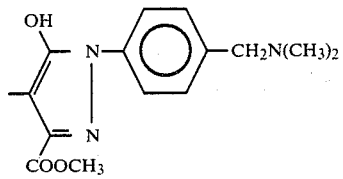 | " | KK$_1$ | b |
| 120 | " | *—CONH— | KK$_1$ | b |
| 121 | 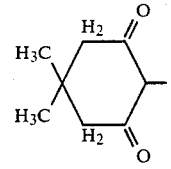 | *—NHCO— | KK$_1$ | b |
| 122 | 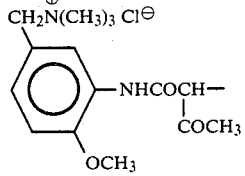 | " | KK$_1$ | b |
| 123 | " | *—CONH— | KK$_2$ | b |

TABLE 4-continued

| Ex. No. | KK$_f$ | —B$_4$— | KK | shade on paper |
|---|---|---|---|---|
| 124 | NHCOCH—COCH$_3$ (on phenyl); CONH(CH$_2$)$_3$N(CH$_3$)$_2$ | " | KK$_2$ | b |
| 125 | " | —$\overset{*}{N}$HCO— | KK$_1$ | b |
| 126 | NHCOCH—COCH$_3$ (on phenyl); SO$_2$NH(CH$_2$)$_3$N(CH$_3$)$_2$ | " | KK$_1$ | b |
| 127 | " | —$\overset{*}{C}$ONH— | KK$_7$ | b |
| 128 | NHCOCH—COCH$_3$ (on phenyl); NH-triazine with HN(CH$_2$)$_3$N(CH$_3$)$_2$ and NH(CH$_2$)$_3$N(CH$_3$)$_2$ | " | KK$_1$ | b |
| 129 | " | —$\overset{*}{N}$HCO— | KK$_1$ | b |
| 130 | HNCOCH—COCH$_3$ (on phenyl); CONH(CH$_2$)$_3$N(C$_2$H$_5$)$_2$ | " | KK$_1$ | b |
| 131 | " | —$\overset{*}{C}$ONH— | KK$_1$ | b |
| 132 | NHCOCH—COCH$_3$ (on phenyl); NH-triazine with HN(CH$_2$)$_3$N(C$_2$H$_5$)$_2$ and NH(CH$_2$)$_3$N(C$_2$H$_5$)$_2$ | " | KK$_1$ | b |
| 133 | " | —$\overset{*}{N}$HCO— | KK$_1$ | b |

TABLE 4-continued

| Ex. No. | KK$_f$ | —B$_4$— | KK | shade on paper |
|---|---|---|---|---|
| 134 | (naphthalene with HO$_3$S and —NHCOCH(COCH$_3$)—) | " | KK$_2$ | b |
| 135 | " | —CONH—* | KK$_1$ | b |
| 136 | (naphthalene with OH, CH$_3$, SO$_3$H, NHCOCH$_3$) | " | KK$_1$ | f |
| 137 | " | —NHCO—* | KK$_1$ | f |
| 138 | (naphthalene with OH, CH$_3$, SO$_3$H) | " | KK$_1$ | f |
| 139 | (naphthalene with OH, CH$_3$, SO$_3$H) | " | KK$_1$ | f |
| 140 | (naphthalimide with N—CH$_3$, CH$_3$, OH) | " | KK$_1$ | f |
| 141 | " | —CONH—* | KK$_1$ | f |
| 142 | (naphthalimide with N—(CH$_2$)$_3$N(CH$_3$)$_2$, CH$_3$, SO$_3$H, OH) | " | KK$_6$ | f |
| 143 | " | —NHCO—* | KK$_2$ | f |
| 144 | (H$_2$NC—N=pyrimidine with H, N, OH, O) | " | KK$_1$ | b |
| 145 | " | —CONH—* | KK$_1$ | b |

TABLE 4-continued

| Ex. No. | KK' | —B₄— | KK | shade on paper |
|---|---|---|---|---|
| 146 | [structure: H₂NC(O)—N=C(NH)—N(H)— pyrimidine with C=O and C—OH] | " | KK₁ | b |
| 147 | " | —*NHCO— | KK₂ | b |
| 148 | [structure: naphthalene with OH, CH₃, SO₃H, and NH— linked to triazine bearing two NH(CH₂)₃N(C₂H₅)₂ groups] | " | KK₁ | f |
| 149 | " | —*CONH— | KK₁ | f |
| 150 | [structure: naphthalene with OH, CH₃, two SO₃H, and NH— linked to triazine bearing two NH(CH₂)₃N(C₂H₅)₂ groups] | " | KK₁ | g |
| 151 | " | —*NHCO— | KK₁ | g |

According to the method described in Examples 63 and 64 further dyestuffs in accordance with the invention may be prepared using one of the following tetrazo components (A) to (C) instead of 4,4'-diaminobenzanilide:

(A) $H_2N-\phi-CONH-\phi-NH_2$ (B) $H_2N-\phi-NHCO-\phi-NH_2$ (C) $H_2N-\phi\;\;\;\;-NHCO-\phi-NH_2$ The dyeing properties of these dyestuffs are similar to those of the dyestuffs in Table 4.

EXAMPLE 152

4.5 Parts of 4-aminoacetanilide are conventionally diazotized at 0°–5° in a diluted hydrochloric acid medium. Subsequently, 17.5 parts of the coupling component of Example 1a are added and a yellow solution is obtained. After coupling having been completed 50 parts 30% hydrochloric acid are added. The mixture is stirred at 95° for two hours to split off the acetyl protecting group. After the acidic hydrolysis is completed a dyestuff corresponding to the formula $$H_2N-\phi-N=N-KK_1$$

is obtained in solution, which dyes paper a yellow shade.

EXAMPLE 153

The dye solution prepared according to Example 152 is carefully neutralized up to pH 5 to 6 by the addition of sodium carbonate. To this solution which is cooled to 0° with ice 5.5 parts cyanuric chloride are added. During the reaction the pH is kept at 5 to 6 by the addition of sodium carbonate. After condensation is completed 11 parts of a compound of the formula

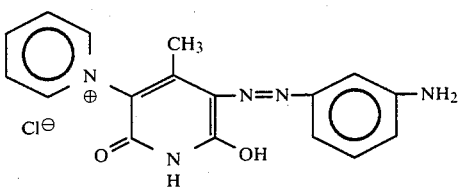

are added. Stirring is effected at 25° to 35° and pH 6 to 7 until the second condensation is completed to form a dyestuff which is precipitated by the addition of sodium hydroxide solution, then filtered and dried. The dyestuff corresponding to the formula

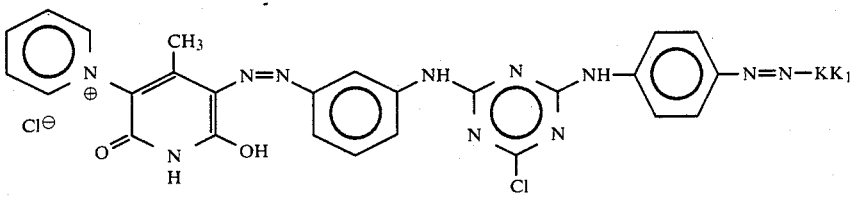

is obtained in form of a yellow powder which in acid addition salt form dyes paper a neutral-yellow shade. Light and wet fastness properties of the paper dyeings are remarkably good.

For the dyestuff described in Example 153 a third condensation step is possible to replace the chlorine atom bound to the triazine ring in analogy with conventional methods comprising reacting to the dyestuff before isolation for example an appropriate amine. Preferred is the reaction with an amine of the aliphatic series and particularly with those amines specifically cited in the description hereinbefore.

EXAMPLES 154–165

In the following Table 5 some dyestuffs of this series where a chlorine atom is present on the triazine ring or may be replaced are listed. They correspond to the general formula

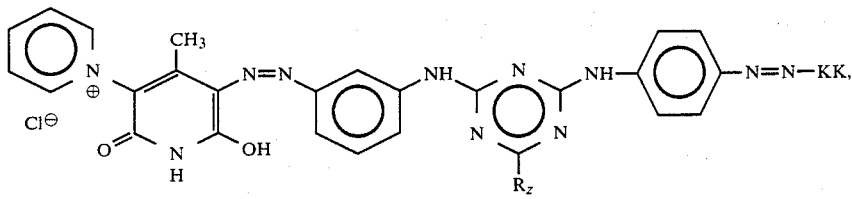

the coupling components KK are as defined in Examples 1 to 5. These dyestuffs (in acid addition salt form) dye paper a yellow shade.

TABLE 5

| Ex. No. | $R_z$ | KK |
|---|---|---|
| 154 | Cl | $KK_2$ |
| 155 | $-NHCH_3$ | $KK_1$ |
| 156 | $-NHC_2H_5$ | $KK_1$ |
| 157 | $-NHCH_2CH_2OH$ | $KK_1$ |
| 158 | $-N(CH_2CH_2OH)_2$ | $KK_1$ |
| 159 | $-NH(CH_2)_3N(C_2H_5)_2$ | $KK_1$ |
| 160 | " | $KK_2$ |
| 161 | $-NH(CH_2)_3N(CH_3)_2$ | $KK_6$ |
| 162 | " | $KK_7$ |

TABLE 5-continued

| Ex. No. | $R_z$ | KK |
|---|---|---|
| 163 | ![NH-phenyl-N(CH3)3+] | $KK_{12}$ |
| 164 | " | $KK_{14}$ |
| 165 | Cl | $KK_{14}$ |

EXAMPLE 166

When the dyestuff solution obtained in Example 152 is diazotized in accordance with conventional methods and reacted with the coupling component of Example 1a a dyestuff having the formula

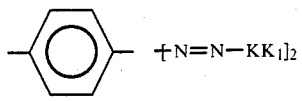

is obtained which dyes paper a clear orange shade.

EXAMPLE 167

12 Parts of 4,4'-diamino-3,3'-dimethoxy-1,1'-diphenyl are diazotized according to conventional methods and are coupled at pH 8 to 9 to 110 parts of the coupling component of Example 1a. An orange dyestuff is formed which is precipitated by the addition of sodium hydroxide solution and filtered. The wet paste obtained is stirred in 400 parts water; to this acetic acid is added in such an amount that the pH is adjusted to 4. The dyestuff goes into solution. 60 Parts sodium acetate and then 55 parts copper sulphate.pentahydrate are added. The resulting mixture is heated to 97° and stirred at this temperature for 20 hours. After this time coppering is complete. The mixture is cooled to 20° and the formed dyestuff is precipitated by the addition of sodium hydroxide solution. Subsequently, it is filtered and dried. The 1:1 copper complex of the disazo dye having the formula

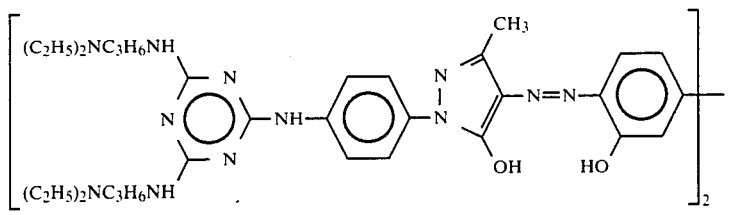

is obtained which in acid addition salt form dyes paper a orange-brown shade. These paper dyeings show perfect light and wet fastnesses.

EXAMPLE 168

27.9 Parts 2-amino-1-hydroxybenzene-4-sulphonic acid-4'-aminophenylamide are dissolved in 150 parts 10% hydrochloric acid and are diazotized (on both amino groups) at 0°–5° with 13.8 parts sodium nitrite in conventional manner. A yellow-brown suspension is formed to which 110 parts of the coupling component of Example 1b are added. Coupling is effected at pH 7 to 8. The resulting dyestuff is precipitated by the addition of sodium hydroxide solution and filtered. The wet presscake is redissolved in 400 parts dimethylformamide. 14.1 Parts $CoSO_4.7H_2O$ (dissolved in 100 parts water) are added keeping the pH at 10 by the addition of 30% sodium hydroxide solution. Subsequently, 9 parts 10% hydrogen peroxide solution are added dropwise.

groups in conventional manner. To the diazo suspension 52.4 parts of the coupling component described in Example 1a are added. Coupling is effected at one side adjusting to pH 4 which is kept by the addition of sodium acetate. After the first coupling is completed, 17.4 parts of 3-methyl-1-phenyl-5-pyrazolone dissolved in 120 parts 5% sodium hydroxide solution are added. By further addition of sodium hydroxide solution the pH is adjusted to 10. The formed disazo dyestuff precipitates completely and is filtered. The wet presscake is suspended in 400 parts water, the pH of the suspension is adjusted to 4 by the addition of acetic acid upon which the dyestuff goes into solution. To this solution 11.5 parts of chromium (III) acetate is added. The solution is refluxed for some hours until metallization is complete. The reaction mixture is cooled to 20° and the dyestuff is precipitated by the addition of sodium hydroxide solution, then filtered and dried. The thus obtained 1:2 chromium complex of the dyestuff having the formula

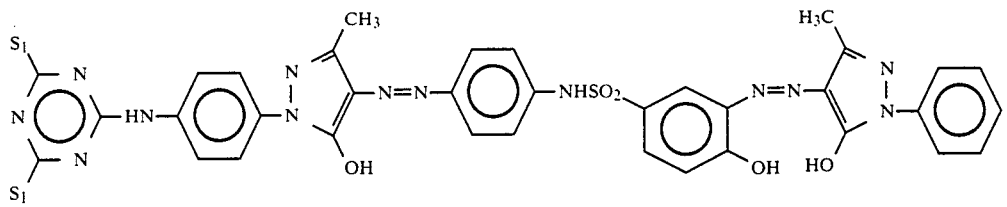

$S_1 = -NHC_3H_6N(C_2H_5)_2$

After metallization is completed the dyestuff is precipitated by diluting the reaction mixture with water and adding sodium hydroxide solution and is then filtered and dried in vacuo at 80°. The thus obtained 1:2 cobalt complex of the compound having the formula dyes leather in orange-red shades. The dyeings have good light fastness.

EXAMPLE 170

12.6 Parts of the dyestuff powder of Example 15 are

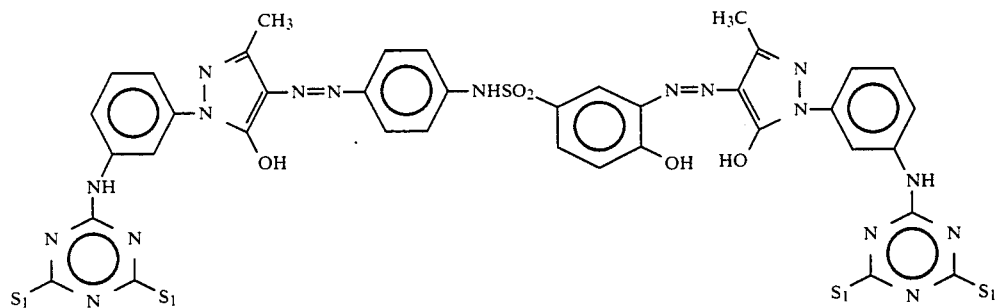

$S_1 = -NHC_3H_6N(C_2H_5)_2$ dyes leather a yellow shade. These dyeings have notable light fastness.

EXAMPLE 169

27.9 Parts 2-amino-1-hydroxybenzene-4-sulphonic acid-4'-aminophenylamide are diazotized on both amino stirred into 300 parts of water and then the mixture is acidified with 2.4 parts glacial acetic acid. The dyestuff dissolves completely. Subsequently, the dyestuff solution is evaporated to dryness. A dyestuff in acid addition salt form having the formula

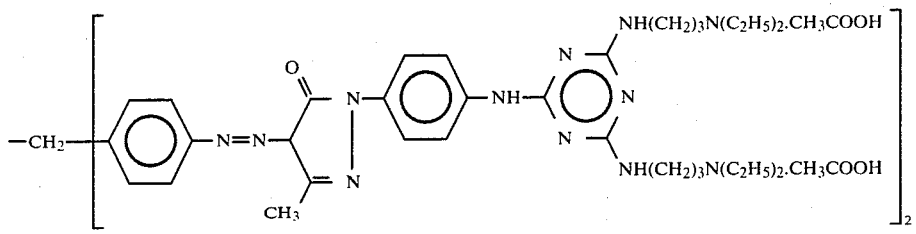

is obtained in powder form which has good solubility in cold water.

Instead of employing the glacial acetic acid of Example 170 hydrochloric acid, sulphuric acid, phosphoric acid, formic acid, lactic acid and other inorganic or preferably organic acids may be used for forming external salts. The dyes of the above Examples, provided that they contain basic groups, may also be converted into acid addition salt form in analogous manner.

EXAMPLE 171

60 parts of the dyestuff salt of Example 170 are added at room temperature to a solution of 20 parts dextrin, 20 parts glacial acetic acid and 400 parts water and are stirred to a homogeneous suspension. By spray drying yellow granulates are obtained which are well soluble in water and dye paper in neutral-yellow shades.

In analogous manner, the dyes of the other Examples may also be converted to granulates.

EXAMPLE 172

20 parts of the dyestuff powder of Example 15 are added to a solvent mixture of 75 parts water and 13 parts glacial acetic acid and are dissolved by heating to 60°. The dyestuff solution is then clear-filtered (employing kieselgur or Hyflo). The filtrate is cooled to room temperature and is adjusted to 120 parts by adding water. A ready-to-use dyestuff solution is obtained which is stable to storage for several months and which neither under warm nor cold conditions allows the dyestuff to be deposited. This dyestuff solution may be used directly (or thinned with water) in dyeing paper whereby paper dyeings of neutral-yellow shades are obtained.

In analogous manner, the dyes of the other Examples may be converted to stable liquid preparations.

In the following examples the application of the dyestuffs of this invention is illustrated.

Application Example A

70 Parts of chemically bleached sulphite cellulose obtained from pinewood and 30 parts of chemically bleached sulphite cellulose obtained from birchwood are ground in 2000 parts of water in a Hollander. 0.5 Parts of the dyestuff from Example 15 (as an acid addition salt, e.g. according to Example 170) are sprinkled into this pulp. Paper is produced from this pulp after mixing for 20 minutes. The absorbent paper which is obtained in this manner is dyed in a neutral-yellow tone. The waste water is practically colourless.

Application Example B 0.5 Parts of the dyestuff from Example 15 (as an acid addition salt, e.g. according to Example 170) are dissolved in 100 parts of hot water and cooled to room temperature. This solution is added to 100 parts of chemically bleached sulphite cellulose which have been ground in a Hollander with 2000 parts of water. Sizing takes place after thorough mixing for 15 minutes. The paper which is produced from this material has a neutral-yellow shade and good light- and wet-fastnesses.

Application Example C

An absorbent length of unsized paper is drawn at 40°–50° through a dyestuff solution having the following composition:
0.5 parts of the dyestuff from Example 15 (as an acid addition salt, e.g. according to Example 170)
0.5 parts of starch and
99.0 parts of water.

The excess dyestuff solution is squeezed out through two rollers. The dried length of paper is dyed in a yellow shade.

The dyestuffs of the remaining Examples may also be used for dyeing according to Application Examples A to C in salt or acid addition salt form or in the form of solid or liquid preparations according to Example 171 or 172.

Application Example D

100 Parts freshly tanned and neutralized chrome leather are agitated for 30 minutes in a vessel with a liquor consisting of 250 parts water at 55° and 0.5 parts of the dyestuff of Examples 63, 168 and 169, respectively, in acid addition salt form, and then treated in the same bath for 30 minutes with 2 parts of an anionic fatty licker based on sulphonated train oil. The leather is then dried and prepared in the normal way, giving a leather evenly dyed in a yellow-orange (yellow and orange-red, respectively) shades.

Application Example E

2 Parts of the dyestuff of Example 63 in acid addition salt form are dissolved in 4000 parts demineralized water at 40°. 100 Parts of a pre-wetted cotton textile substrate are added, and the bath is raised to boiling point over 30 minutes and held at the boil for one hour. Any water which evaporates during dyeing is replaced continuously. After rinsing and drying, a yellow-orange dyeing is obtained having good light- and wet-fastnesses. The dye exhausts practically totally, and the waste water is almost colourless.

What we claim is:

1. A metal-free compound of the formula

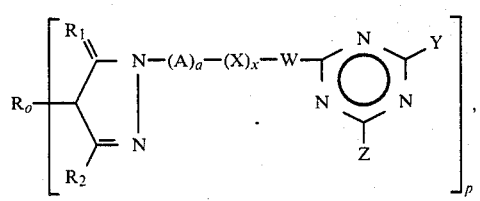

a 1:1 or 1:2 metal complex of a metallizable metal-free azo compound of said formula or a salt or acid addition salt of a metal-free compound of said formula or of a 1:1 or 1:2 metal complex of a metallizable metal-free azo compound of said formula,
wherein
$R_o$ is R or —N=N—T—N=N—,
wherein T is the radical of a tetrazo component,
each Y is independently hydroxy; $C_{1-4}$alkoxy; phenoxy; amino; an aliphatic, cycloaliphatic, aromatic or heterocyclic amino group; Z or

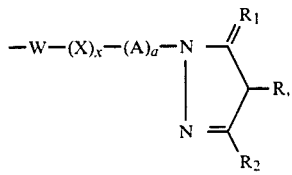

and p is 1 when $R_o$ is R and is 2 when $R_o$ is —N=N—T—N=N—,
wherein
each A is independently phenylene; naphthylene; phenylene-phenylene; or phenylene, naphthylene or phenylene-phenylene each aromatic ring of which is substituted by 1 or 2 substituents selected from halo, nitro, $C_{1-4}$alkyl, $C_{1-4}$alkoxy, carboxy and sulfo,
each R is independently hydrogen or D—N=N—, wherein D is the radical of a diazo component,
each $R_1$ is independently O, NH or S,
each $R_2$ is independently $C_{1-4}$alkyl, $C_{1-4}$alkoxy, —COOR₃, —CONR₄R₅ or —CO—Z,
wherein $R_3$ is hydrogen, $C_{1-4}$alkyl, phenyl or cyclohexyl,
each of $R_4$ and $R_5$ is independently hydrogen; $C_{1-4}$alkyl; $C_{2-4}$alkyl monosubstituted in other than the the 1-position by hydroxy; or monosubstituted by cyano or chloro; phenyl; phenyl substituted by 1 or 2 substituents selected from methyl, ethyl, methoxy and ethoxy; phenyl($C_{1-4}$alkyl) or phenyl($C_{1-4}$alkyl) the phenyl group of which is substituted by 1 or 2 substituents selected from methyl, ethyl, methoxy and ethoxy; or cyclohexyl, and
Z is as defined below,
each W is independently —NR₆— or

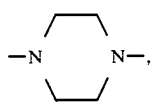

wherein $R_6$ is hydrogen; $C_{1-4}$alkyl; $C_{2-4}$alkyl monosubstituted in other than the 1-position by hydroxy or monosubstituted by cyano, chloro or $C_{1-4}$alkoxy; phenyl($C_{1-4}$alkyl) or cyclohexyl,
each X is independently linear or branched $C_{1-6}$alkylene, —*CONH-linear or branched $C_{1-6}$alkylene- or —*SO₂NH-linear or branched $C_{1-6}$alkylene, wherein the * denotes the atom attached to the —(A)ₐ— radical,
each Z is independently an N-bonded organic radical containing 1 to 5 nitrogen atoms at least one of which has basic character or forms an ammonium cation,
each a is independently 0 or 1,
each x is independently 0 or 1, with the proviso that the sum of each adjacent a and x is 1 or 2, and
each halo is independently fluoro, chloro, bromo or iodo,
or a mixture thereof.

2. A metal-free compound, a 1:1 or 1:2 metal complex or a salt or acid addition salt according to claim 1
wherein each Y is independently hydroxy; $C_{1-4}$alkoxy; phenoxy; —NR$_a$R$_a$; $C_{5-6}$cycloalkylamino; $C_{5-6}$cycloalkylamino the cycloalkyl ring of which is substituted by 1 or $C_{1-2}$alkyl groups; anilino; anilino the phenyl ring of which is substituted by 1 or 2 substituents selected from halo, $C_{1-4}$alkyl, $C_{1-4}$alkoxy, hydroxy and phenoxy; morpholino; piperidino; Z or

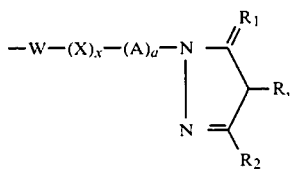

wherein each $R_a$ is independently hydrogen; $C_{1-4}$alkyl; $C_{1-4}$alkyl monosubstituted by halo or $C_{2-4}$alkyl monosubstituted in other than the 1-position by hydroxy, and
each Z is independently

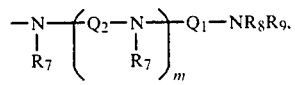

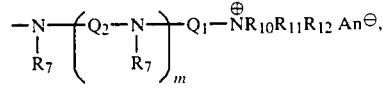

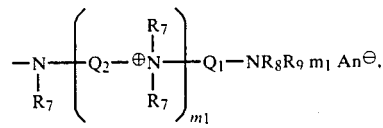

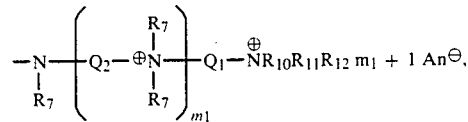

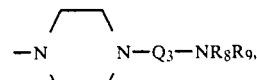

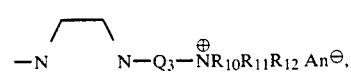

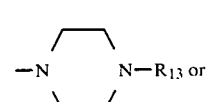

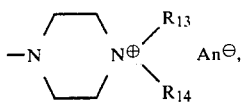

wherein
$Q_1$ is linear or branched $C_{2-8}$alkylene, linear or branched $C_{1-6}$alkylene-$C_6$ or $C_{10}$arylene, $C_6$ or $C_{10}$arylene or —*NHCO—CH$_2$—,
wherein the * denotes the atom attached to the —NR$_7$— radical,
$Q_2$ is linear or branched $C_{2-8}$alkylene, linear or branched $C_{1-6}$alkylene-$C_6$ or $C_{10}$arylene or $C_6$ or $C_{10}$arylene,
$Q_3$ is linear or branched $C_{2-8}$alkylene,
Each $R_7$ is independently hydrogen or $C_{1-4}$alkyl,
each of $R_8$ and $R_9$ is independently hydrogen; $C_{1-6}$alkyl; $C_{2-6}$alkyl monosubstituted in other than the 1-position by hydroxy or monosubstituted by cyano; phenyl($C_{1-3}$alkyl); phenyl($C_{1-3}$alkyl) the phenyl group of which is substituted by 1 to 3 substituents selected from chloro, $C_{1-4}$alkyl and $C_{1-4}$alkoxy; $C_{5-6}$cycloalkyl or $C_{5-6}$cycloalkyl substituted by 1 to 3 $C_{1-4}$alkyl groups, or
—NR$_8$R$_9$ is pyrrolidino, piperidino morpholino, piperazino or N-methylpiperazino,
each of $R_{10}$ and $R_{11}$ is independently $C_{1-6}$alkyl; $C_{2-6}$alkyl monosubstituted in other than the 1-position by hydroxy or monosubstituted by cyano; phenyl($C_{1-3}$alkyl); phenyl($C_{1-3}$alkyl) the phenyl group of which is substituted by 1 to 3 substituents selected from chloro, $C_{1-4}$alkyl and $C_{1-4}$alkoxy; $C_{5-6}$cycloalkyl or $C_{5-6}$cycloalkyl substituted by 1 to 3 $C_{1-4}$alkyl groups, and
$R_{12}$ is $C_{1-4}$alkyl or benzyl, or
—N$^⊕$R$_{10}$R$_{11}$R$_{12}$ is pyridinium, pyridinium substituted by 1 or 2 methyl groups,

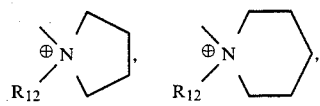

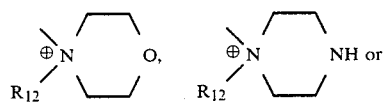

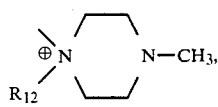

wherein
$R_{12}$ is as defined above,
$R_{13}$ is hydrogen, $C_{1-6}$alkyl or $C_{1-6}$alkyl monosubstituted in other than the 1-position by hydroxy or monosubstituted by cyano, chloro or phenyl,
$R_{14}$ is $C_{1-6}$alkyl or $C_{1-6}$alkyl substituted in other than the 1-position by hydroxy or substituted by cyano or chloro,
each An$^⊖$ is a non-chromophoric anion, m is 0, 1, 2 or 3, and m$_1$ is 1, 2, or 3.

3. A metal-free compound, a 1:1 or 1:2 metal complex or a salt or acid addition salt according to claim 2 wherein each $R_1$ is independently O or NH, and
each $R_2$ is independently methyl, carboxy, methoxycarbonyl, carbamoyl or —CO—Zd,
wherein
Zd is —NH—Q$_{1c}$—NR$_{8c}$R$_{9c}$ or

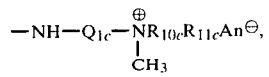

wherein
$Q_{1c}$ is ethylene or 1,3-propylene, and
each of $R_{8c}$, $R_{9c}$, $R_{10c}$ and $R_{11c}$ is independently methyl or ethyl.

4. A metal-free compound, a 1:1 or 1:2 metal complex or a salt or acid addition salt according to claim 3 wherein
each $R_1$ is O, and
each $R_2$ is methyl.

5. A metal-free compound, a 1:1 or 1:2 metal complex or a salt or acid addition salt according to claim 2 wherein
each A is independently 1,3-phenylene or 1,4-phenylene,
each W is independently is —NH—, —NCH$_3$— or

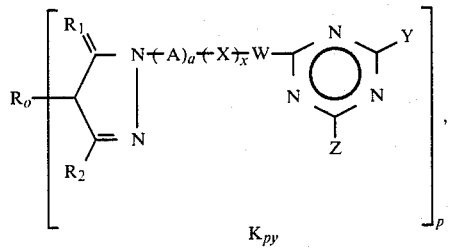

each a is 1, and
each x is 0.

6. A metal-free compound, a 1:1 or 1:2 metal complex or a salt or acid addition salt according to claim 2 wherein
each z is independently —NR$_{7a}$—Q$_{1b}$—NR$_{8b}$R$_{9b}$, —NR$_{7a}$—Q$_{1b}$—N$^⊕$R$_{10b}$R$_{11b}$R$_{12a}$An$^⊖$,

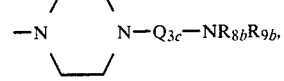

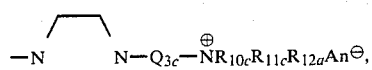

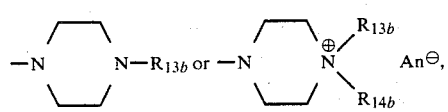

wherein
$Q_{1b}$ is linear $C_{2-6}$alkylene,
$Q_{3c}$ is ethylene or 1,3-propylene,
$R_{7a}$ is hydrogen or methyl,
each of $R_{8b}$ and $R_{9b}$ is independently hydrogen, $C_{1-4}$alkyl or 2-hydroxyethyl, or —NR$_{8b}$R$_{9b}$ is morpholino, piperidino, piperazino or N-methylpiperazino, each of R$_{10b}$ and R$_{11b}$ is independently C$_{1-4}$alkyl or 2-hydroxyethyl, each of R$_{10c}$ and R$_{11c}$ is independently methyl or ethyl, R$_{12a}$ is methyl, ethyl or benzyl, or —N$^{\oplus}$R$_{10b}$R$_{11b}$R$_{12a}$ is pyridinium, R$_{13b}$ is hydrogen, methyl or ethyl, and R$_{14b}$ is methyl, ethyl or 2-hydroxyethyl.

7. A metal-free non-azo compound according to claim 2,
or a salt or acid addition salt thereof,
wherein
R$_0$ is hydrogen, and
p is 1.

8. A metal-free non-azo compound according to claim 7 having the formula

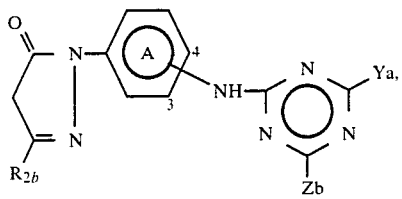

or a salt or acid addition salt thereof,
wherein
R$_{2b}$ is methyl, carboxy, methoxycarbonyl, carbamoyl or —CO—Zd,
wherein Zd is —NH—Q$_{1c}$—NR$_{8c}$R$_{9c}$ or

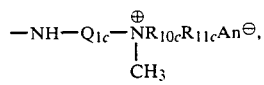

wherein
Q$_{1c}$ is ethylene or 1,3-propylene, and
each of R$_{8c}$, R$_{9c}$, R$_{10c}$ and R$_{11c}$ is independently methyl or ethyl,
Ya is hydroxy, methoxy, phenoxy, amino, C$_{1-4}$alkylamino, C$_{2-4}$hydroxyalkylamino the hydroxy group of which is in other than the 1-position, di-(C$_{1-2}$alkyl)amino, di-(C$_{2-4}$hydroxyalkyl)amino each hydroxy group of which is in other than the 1-position, anilino, morpholino, piperidino, Zb or

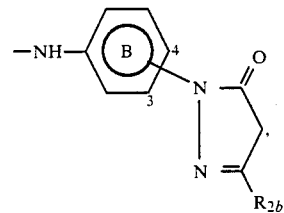

wherein R$_{2b}$ is as defined above, and the pyrazolone ring is in the 3- or 4-position of Ring B, and
the —NH— radical is in the 3- or 4-position of Ring A,
wherein
each Zb is independently —NR$_{7a}$—Q$_{1b}$—NR$_{8b}$R$_{9b}$, —NR$_{7a}$—Q$_{1b}$—N$^{\oplus}$R$_{10b}$R$_{11b}$R$_{12a}$An$^{\ominus}$,

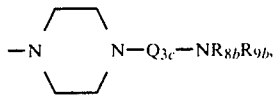

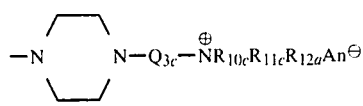

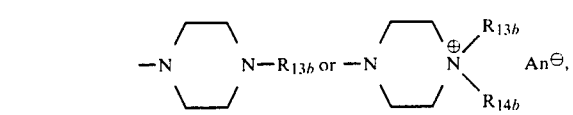

wherein
Q$_{1b}$ is linear C$_{2-6}$alkylene,
Q$_{3c}$ is ethylene or 1,3-propylene
R$_{7a}$ is hydrogen or methyl,
each of R$_{8b}$ and R$_{9b}$ is independently hydrogen, C$_{1-4}$alkyl or 2-hydroxyethyl, or
—NR$_{8b}$R$_{9b}$ is morpholino, piperidino, piperazino or N-methylpiperazino,
each of R$_{10b}$ and R$_{11b}$ is independently C$_{1-4}$-alkyl or 2-hydroxyethyl,
each of R$_{10c}$ and R$_{11c}$ is independently methyl or ethyl,
R$_{12a}$ is methyl, ethyl or benzyl, or
—N$^{\oplus}$R$_{10b}$R$_{11b}$R$_{12a}$ is pyridinium,
R$_{13b}$ is hydrogen, methyl or ethyl, and
R$_{14b}$ is methyl, ethyl or 2-hydroxyethyl,
wherein
each An$^{\ominus}$ is a non-chromophoric anion 9. A metal-free non-azo compound according to claim 8,
or a salt or acid addition salt thereof,
wherein
R$_{2b}$ is methyl,
Ya is Zd, and
Zb is Zd.

10. A metal-free azo compound according to claim 2 having the formula

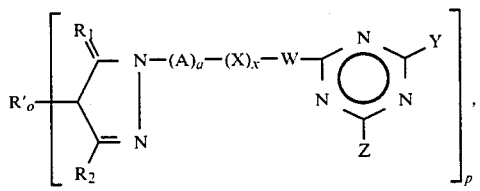

a 1:1 or 1:2 metal complex of a metallizable metal-free azo compound of said formula or a salt or acid addition salt of a metal-free azo compound of said formula or of a 1:1 or 1:2 metal complex of a metallizable metal-free azo compound of said formula,
wherein
R$_o'$ is D—N=N— or —N=N—T—N=N—, and
p is 1 when R$_o'$ is D—N=N— and is 2 when R$_o'$ is —N=N—T—N=N—.

11. A metal-free azo compound according to claim 10 having the formula

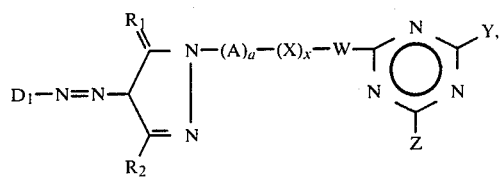

a 1:1 or 1:2 metal complex of a metallizable metal-free azo compound of said formula or a salt or acid addition salt of a metal-free azo compound of said formula or of a 1:1 or 1:2 metal complex of a metallizable metal-free azo compound of said formula,
wherein
$D_1$ is —$A_t$—N=N—$K_t$, $D_{t1}$—N=N—$D_{t2}$—N=N—$D_{t3}$—,

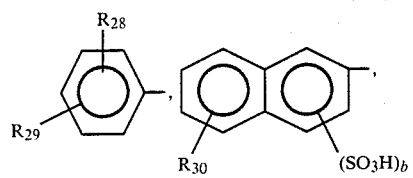

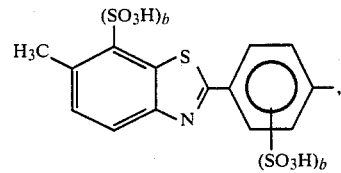

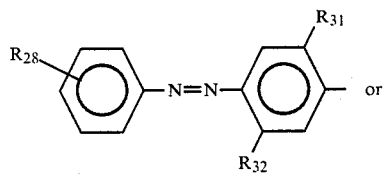

wherein
$A_t$ is the radical of a tetrazo component,
$D_{t1}$ is

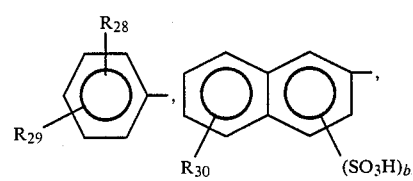

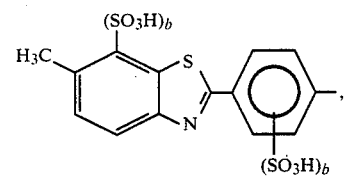

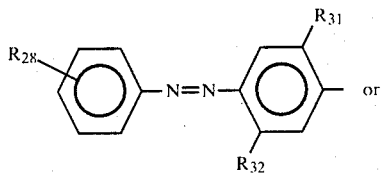

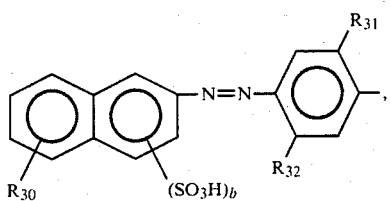

each of $D_{t2}$ and $D_{t3}$ is independently 1,4-phenylene; 1,4-phenylene monosubstituted by methyl, methoxy, acetamido, ureido or trimethylammoniumacetamido $An^{\ominus}$; or 1,4-phenylene substituted by two methyl groups, by two methoxy groups or by one methyl group and one methoxy group, and
$K_t$ is

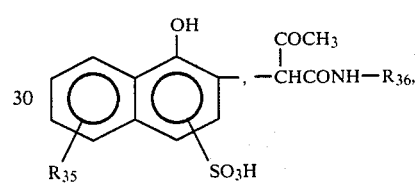

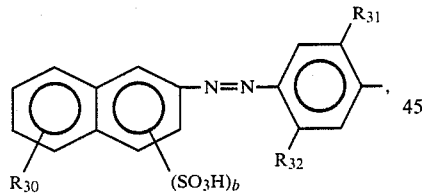

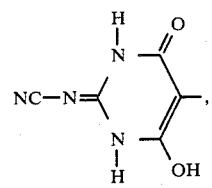

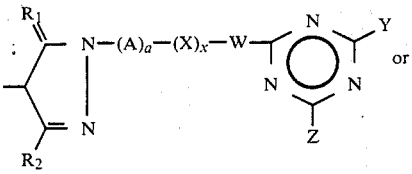

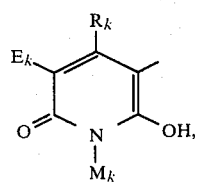

wherein
$E_k$ is hydrogen, cyano, —COOR$_{15}$, —CONR$_{16}$R$_{17}$, sulfo, —CH$_2$R$_{18}$,

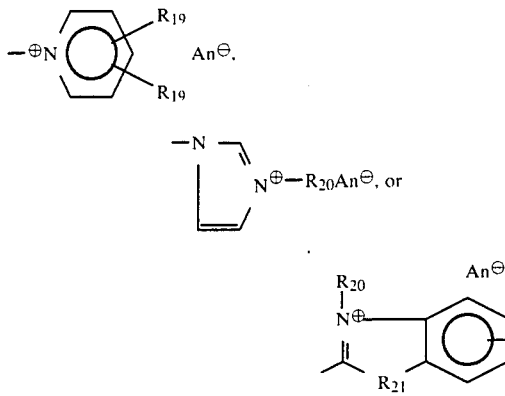

$M_k$ is hydrogen; $-NR_{23}R_{24}$; $C_{1-6}$alkyl; $C_{2-4}$hydroxyalkyl the hydroxy group of which is in other than the 1-position; $(C_{1-4}$alkoxy)$C_{1-4}$alkyl; sulfo($C_{1-4}$alkyl); $C_{5-6}$cycloalkyl; $C_{5-6}$cycloalkyl substituted by 1 to 3 $C_{1-4}$alkyl groups; phenyl; phenyl substituted by 1 to 3 substituents selected from $C_{1-4}$alkyl, $C_{1-4}$alkoxy and halo; phenyl($C_{1-3}$alkyl); phenyl($C_{1-3}$alkyl) the phenyl group of which is substituted by 1 to 3 substituents selected from $C_{1-4}$alkyl, $C_{1-4}$alkoxy and halo; $-V_1-NR_{25}R_{26}$ or $-V_2-N^\oplus R_{25}R_{26}R_{27}An^\ominus$, $R_k$ is hydrogen; $C_{1-4}$alkyl; sulfomethyl; $C_{5-6}$cycloalkyl; phenyl; phenyl substituted by 1 or 2 substituents selected from methyl, ethyl, methoxy, ethoxy and chloro; benzyl; phenylethyl; benzyl or phenylethyl the phenyl group of which is substituted by 1 or 2 substituents selected from methyl, ethyl, methoxy, ethoxy and chloro; $C_{1-4}$alkylamino or benzothiazolyl-2, $R_{35}$ is hydrogen or acetamido, $R_{36}$ is sulfonaphthyl-1 or

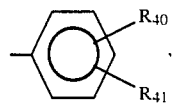

$R_{37}$ is hydroxy or amino,
$R_{38}$ is methyl, phenyl, carboxy, carboxymethyl or methoxycarbonyl, and
$R_{39}$ is hydrogen, allyl,

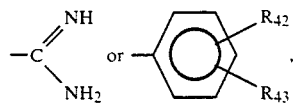

wherein
$R_{15}$ is $C_{1-6}$alkyl or phenyl($C_{1-3}$alkyl),
$R_{18}$ is sulfo or $-NR_{16}R_{17}$,
each $R_{19}$ is independently hydrogen, $C_{1-4}$alkyl, $-NR_{16}R_{17}$ or $-CONR_{16}R_{17}$,
$R_{20}$ is $C_{1-4}$alkyl,
$R_{21}$ is $-S-$, $-O-$ or $-NR_{16}-$,
$R_{22}$ is hydrogen or $C_{1-4}$alkyl,
each of $R_{23}$, $R_{24}$, $R_{25}$ and $R_{26}$ is independently hydrogen; $C_{1-6}$alkyl; $C_{2-6}$alkyl monosubstituted in other than the 1-position by hydroxy or monosubstituted by cyano or halo; phenyl; phenyl substituted by 1 to 3 substituents selected from chloro, $C_{1-4}$alkyl and $C_{1-4}$alkoxy; phenyl($C_{1-3}$alkyl); phenyl($C_{1-3}$alkyl) the phenyl group of which is substituted by 1 to 3 substituents selected from chloro, $C_{1-4}$alkyl and $C_{1-4}$alkoxy; $C_{5-6}$cycloalkyl or $C_{5-6}$cycloalkyl substituted by 1 to 3 $C_{1-4}$alkyl groups, with the proviso that at least one of $R_{25}$ and $R_{26}$ in the group of the formula $-V_1-NR_{25}R_{26}$ is other than hydrogen, or $-NR_{23}R_{24}$ is an unsubstituted 5- or 6-membered saturated ring containing 1 to 3 hetero atoms or a 5- or 6-membered saturated ring containing 1 to 3 hetero atoms which is substituted by 1 to 3 $C_{1-4}$alkyl groups, or $-NR_{25}R_{26}$ is an unsubstituted 5- or 6-membered saturated ring containing 1 to 3 hetero atoms or a 5- or 6-membered saturated ring containing 1 to 3 hetero atoms which is substituted by 1 to 3 $C_{1-4}$alkyl groups, $R_{27}$ is $C_{1-4}$alkyl or phenyl($C_{1-3}$alkyl), or $-N^\oplus R_{25}R_{26}R_{27}$ is pyridinium; pyridinium substituted by 1 to 3 $C_{1-4}$alkyl groups; an unsubstituted 5- or 6-membered partially unsaturated ring containing 1 to 3 hetero atoms or a 5- or 6-membered partially unsaturated ring containing 1 to 3 hetero atoms which is substituted by 1 to 3 $C_{1-4}$alkyl groups, $R_{28}$ is hydrogen, $C_{1-2}$alkyl, $C_{1-2}$alkoxy, acetamido, carboxy, sulfo, trimethylammonium $An^\ominus$ or trimethylammoniummethyl $An^\ominus$, $R_{29}$ is hydrogen or $C_{1-2}$alkyl, $R_{30}$ is sulfo, sulfamoyl, aminomethyl or trimethylammoniummethyl $An^\ominus$, $R_{31}$ is hydrogen, $C_{1-2}$alkyl or $C_{1-2}$alkoxy, $R_{32}$ is hydrogen, $C_{1-2}$alkyl, $C_{1-2}$alkoxy, acetamido, ureido or trimethylammoniumacetamido $An^\ominus$, $R_{40}$ is hydrogen or methoxy, $R_{41}$ is hydrogen, trimethylammoniummethyl $An^\ominus$, $-CONH-Q_{3c}-NR_{8b}R_{9b}$, $-SO_2NH-Q_{3c}-NR_{8b}R_{9b}$ or -NH—⟨triazine with Yb and Zc⟩.

wherein Yb is hydroxy, amino, $C_{1-2}$alkylamino, $C_{2-4}$hydroxyalkylamino the hydroxy group of which is in other than the 1-position, di-($C_{2-4}$hydroxyalkyl)amino each hydroxy group of which is in other than the 1-position or Zc, $R_{42}$ is hydrogen, halo, $C_{1-2}$alkyl, $C_{1-2}$alkoxy, sulfo, trimethylammoniumacetamido $An^\ominus$, trimethylammonium $An^\ominus$, trimethylammoniummethyl $An^\ominus$ or $-CH_2-NR_{8b}R_{9b}$, $R_{43}$ is hydrogen or halo, $V_1$ is linear or branched $C_{1-6}$alkylene or linear or branched $C_{2-6}$alkenylene, $V_2$ is linear or branched $C_{2-6}$alkylene or linear or branched $C_{2-6}$alkenylene, and b is 0 or 1, wherein each $R_{16}$ and $R_{17}$ is independently hydrogen or $C_{1-4}$alkyl, and each Zc is independently $-NH-Q_{1c}-NR_{8b}R_{9b}$, $-NH-Q_{1c}-N^\oplus R_{10b}R_{11b}R_{12a} An^\ominus$ or

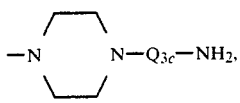

wherein
each $Q_{1c}$ and $Q_{3c}$ is independently ethylene or 1,3-propylene, each $R_{8b}$ and $R_{9b}$ is independently hydrogen, $C_{1-4}$alkyl or 2-hydroxyethyl, or —$NR_{8b}R_{9b}$ is morpholino, piperidino, piperazino or N-methylpiperazino, each $R_{10b}$ and $R_{11b}$ is independently $C_{1-4}$alkyl or 2-hydroxyethyl, $R_{12a}$ is methyl, ethyl or benzyl, or —$N^{\oplus}R_{10b}R_{11b}R_{12a}$ is pyridinium, and each $An^{\ominus}$ is a non-chromophoric anion.

12. A metal free azo compound according to claim 11 having the formula

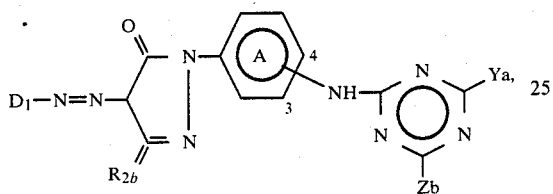

a 1:1 or 1:2 metal complex of a metallizable metal-free azo compound of said formula or a salt or acid addition salt of a metal-free azo compound of said formula or of a 1:1 or 1:2 metal complex of a metallizable metal-free azo compound of said formula,
wherein
$R_{2b}$ is methyl, carboxy, methoxycarbonyl, carbamoyl or —CO—Zd,
wherein
Zd is wherein Zd is —NH—$Q_{1c}$—$NR_{8c}R_{9c}$ or

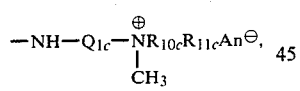

wherein
$Q_{1c}$ is ethylene or 1,3-propylene, and
each of $R_{8c}$, $R_{9c}$, $R_{10c}$ and $R_{11c}$ is independently methyl or ethyl,
Ya is hydroxy, methoxy, phenoxy, amino, $C_{1-4}$alkylamino, $C_{2-4}$hydroxyalkylamino the hydroxy group of which is in other than the 1-position, di-($C_{1-2}$alkyl)amino, di-($C_{2-4}$hydroxyalkyl)amino each hydroxy group of which is in other than the 1-position, anilino, morpholino, piperidino, Zb or

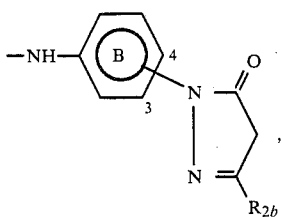

wherein
$R_{2b}$ is as defined above, and the pyrazolone ring is in the 3- or 4-position of Ring B, and the —NH— radical is in the 3- or 4-position of Ring A,
wherein
each Zb is independently —$NR_{7a}$—$Q_{1b}$—$NR_{8b}R_{9b}$, —$NR_{7a}$—$Q_{1b}$—$N^{\oplus}R_{10b}R_{11b}R_{12a}An^{\ominus}$,

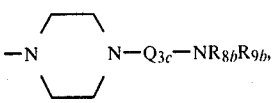

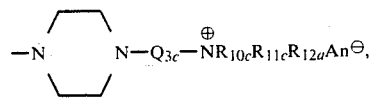

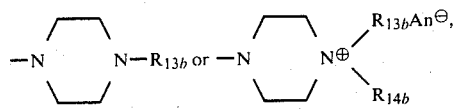

wherein
$Q_{1b}$ is linear $C_{2-6}$alkylene,
$Q_{3c}$ is ethylene or 1,3-propylene,
$R_{7a}$ is hydrogen or methyl,
each of $R_{8b}$ and $R_{9b}$ is independently hydrogen, $C_{1-4}$alkyl or 2-hydroxyethyl, or —$NR_{8b}R_{9b}$ is morpholino, piperidino, piperazino or N-methylpiperazino, each of $R_{10b}$ and $R_{11b}$ is independently $C_{1-4}$alkyl or 2-hydroxyethyl, each of $R_{10c}$ and $R_{11c}$ is independently methyl or ethyl, $R_{12a}$ is methyl, ethyl or benzyl, or —$N^{\oplus}R_{10b}R_{11b}R_{12a}$ is pyridinium,
$R_{13b}$ is hydrogen, methyl or ethyl, and
$R_{14b}$ is methyl, ethyl or 2-hydroxyethyl,
wherein
each $An^{\ominus}$ is a non-chromophoric anion.

13. A metal-free azo compound, a 1:1 or 1:2 metal complex or a salt or acid addition salt according to claim 12
wherein
$D_1$ is

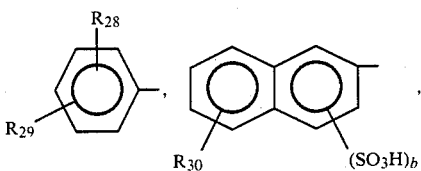

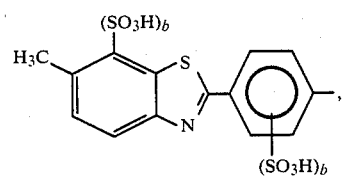

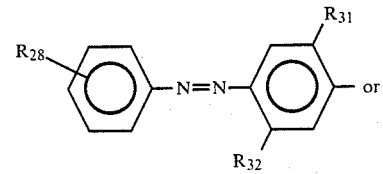

-continued

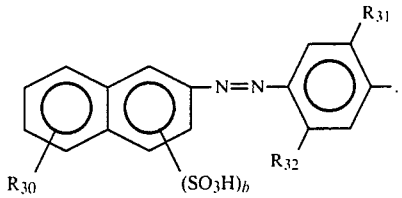

14. The compound according to claim 13 having the formula

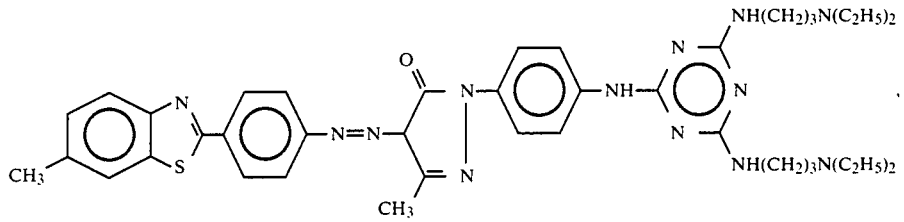

or an acid addition salt thereof.

15. The compound according to claim 13 having the formula

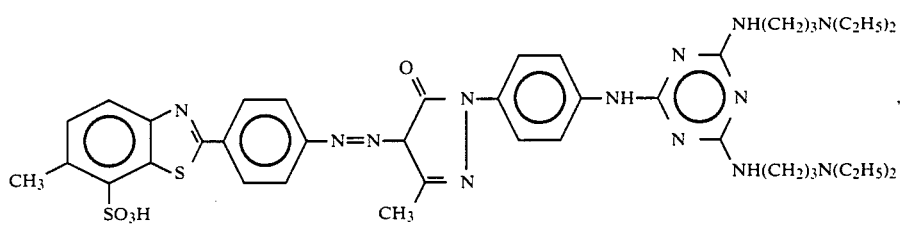

or a salt or an acid addition salt thereof.

16. The compound according to claim 13 having the formula

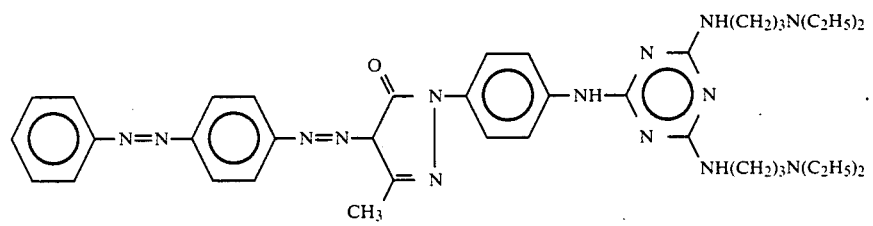

or an acid addition salt thereof.

17. A metal-free azo compound, a 1:1 or 1:2 metal complex or a salt or acid addition salt according to claim 33 wherein
$D_1$ is $-A_{ta}-N=N-K_{ta}$,
wherein $A_{ta}$ is

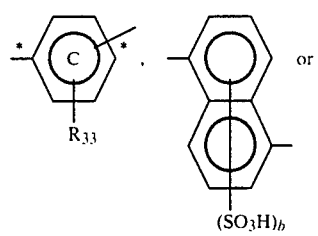

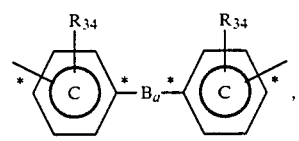

wherein $B_a$ is a direct bond, $-O-$, $-S-$, $-NH-$, $-(CH_2)_c-$, $-NHCO-$, $-NHCONH-$, $-CH=CH-$,

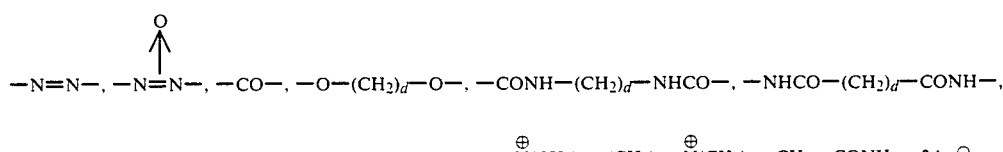

$-N=N-$, $-N\overset{O}{\overset{\uparrow}{=}}N-$, $-CO-$, $-O-(CH_2)_d-O-$, $-CONH-(CH_2)_d-NHCO-$, $-NHCO-(CH_2)_d-CONH-$, $-NHCO-CH=CH-CONH-$, $-NHCO-CH_2-\overset{\oplus}{N}(CH_3)_2-(CH_2)_e-\overset{\oplus}{N}(CH_3)_2-CH_2-CONH-\ 2An^{\ominus}$.

-continued

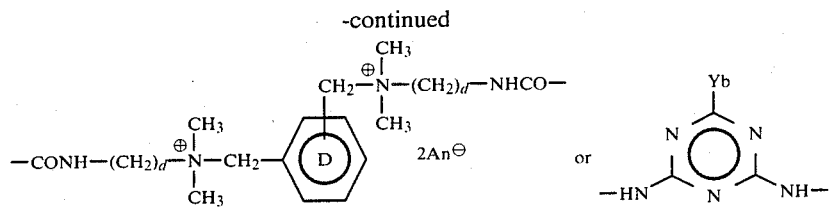

or

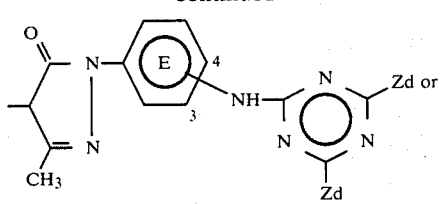

wherein
c is 1, 2 or 3,
each d is 2 or 3, e is 2, 3 or 4, and
the two groups attached to Ring D are meta or para to each other,
$R_{33}$ is hydrogen, halo, $C_{1-4}$alkyl, $C_{1-4}$alkoxy, cyano, carbamoyl, $(C_{1-4}$alkyl)carbonylamino, ureido, carboxy or sulfo,
each $R_{34}$ is independently hydrogen, halo, cyano, $C_{1-4}$alkyl, $C_{1-4}$alkoxy, carboxy or sulfo, and
the two bonds denoted by an * attached to each Ring C are meta or para to each other, and
$K_{ta}$ is

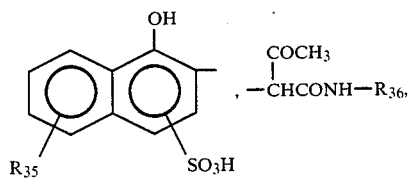

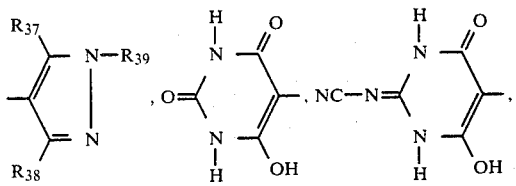

-continued

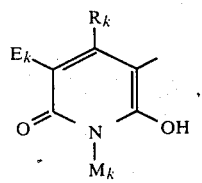

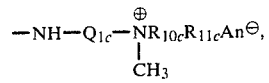

wherein
each Zd is $-NH-Q_{1c}-NR_{8c}R_{9c}$ or $$-NH-Q_{1c}-\overset{\oplus}{\underset{CH_3}{N}}R_{10c}R_{11c}An^{\ominus},$$

wherein each of $R_{8c}$, $R_{9c}$, $R_{10c}$ and $R_{11c}$ is independently methyl or ethyl,
with the proviso that the two Zd groups are identical, and
the —NH— radical is in the 3- or 4-position of Ring E.

18. The compound according to claim 17 having the formula

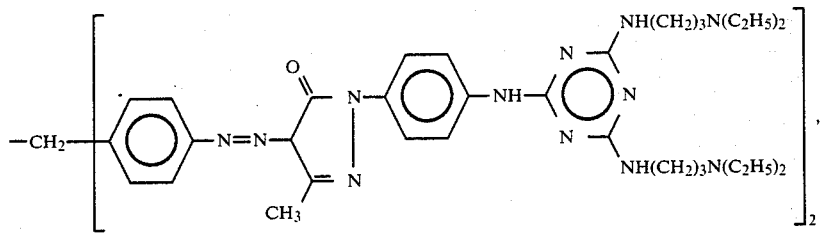

or an acid addition salt thereof.

19. The compound according to claim 17 having the formula

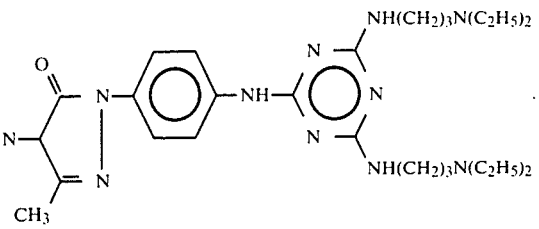
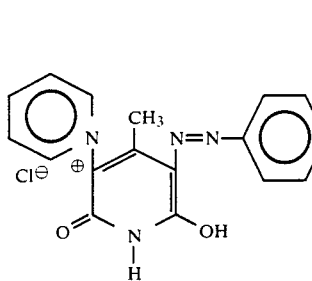
20. The compound according to claim 9 having the formula
* * * * *